(12) United States Patent
Hagiwara

(10) Patent No.: US 12,268,558 B2
(45) Date of Patent: Apr. 8, 2025

(54) ELECTRONIC ENDOSCOPE SYSTEM

(71) Applicant: HOYA CORPORATION, Tokyo (JP)

(72) Inventor: Masayuki Hagiwara, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 344 days.

(21) Appl. No.: 17/801,622

(22) PCT Filed: Jul. 19, 2021

(86) PCT No.: PCT/JP2021/027018
§ 371 (c)(1),
(2) Date: Aug. 23, 2022

(87) PCT Pub. No.: WO2022/064826
PCT Pub. Date: Mar. 31, 2022

(65) Prior Publication Data
US 2023/0080349 A1 Mar. 16, 2023

(30) Foreign Application Priority Data
Sep. 24, 2020 (JP) ................... 2020-159687

(51) Int. Cl.
*A61B 8/08* (2006.01)
*A61B 8/00* (2006.01)
(Continued)

(52) U.S. Cl.
CPC .............. *A61B 8/5269* (2013.01); *A61B 8/12* (2013.01); *A61B 8/14* (2013.01); *A61B 8/463* (2013.01)

(58) Field of Classification Search
CPC .. A61B 8/12; A61B 8/14; A61B 8/463; A61B 8/5207; A61B 8/5269
See application file for complete search history.

(56) References Cited

U.S. PATENT DOCUMENTS

2012/0065509 A1   3/2012  Ziv-Ari et al.
2018/0317883 A1*  11/2018 Huhtamaki ......... G01S 7/52079
2020/0294230 A1   9/2020  Honjo et al.

FOREIGN PATENT DOCUMENTS

JP   2004-363997 A   12/2004
JP   2007-61431 A    3/2007
(Continued)

OTHER PUBLICATIONS

International Search Report issued in International Bureau of WIPO Patent Application No. PCT/JP2021/027018, dated Aug. 24, 2021, along with an English translation thereof.
(Continued)

*Primary Examiner* — Amelie R Davis
(74) *Attorney, Agent, or Firm* — GREENBLUM & BERNSTEIN, P.L.C.

(57) ABSTRACT

An electronic endoscope system according to a first embodiment includes an electronic endoscope, a captured image processor, and an ultrasonic image processor. The electronic endoscope has, at a distal tip thereof, an image sensor, and an ultrasonic probe that repeatedly applies ultrasonic waves to sequentially obtain echo signals. The ultrasonic image processor has a noise detection unit that detects a noise component which is contained in a first echo signal among the echo signals and which is periodically generated at or above a preset threshold level, and a noise inhibition unit that generates a noise inhibition component which, by being added to a second echo signal outputted after the first echo signal, inhibits generation of the noise component in the second echo signal, and that adds the noise inhibition component to the second echo signal.

9 Claims, 17 Drawing Sheets

(51) Int. Cl.
    *A61B 8/12*     (2006.01)
    *A61B 8/14*     (2006.01)

(56) References Cited

FOREIGN PATENT DOCUMENTS

| | | |
|---|---|---|
| JP | 2008-245705 A | 10/2008 |
| JP | 2012-55692 A | 3/2012 |
| JP | 2014-3801 A | 1/2014 |
| JP | 2017-80040 A | 5/2017 |
| JP | 2018-191799 | 12/2018 |
| JP | 2019-76707 A | 5/2019 |
| JP | 2020-146285 A | 9/2020 |

OTHER PUBLICATIONS

Jun. 20, 2023 Notice of Reasons for Refusal in corresponding Japanese Patent Application No. 2022-551159 and English translation thereof.

\* cited by examiner

FIG. 5
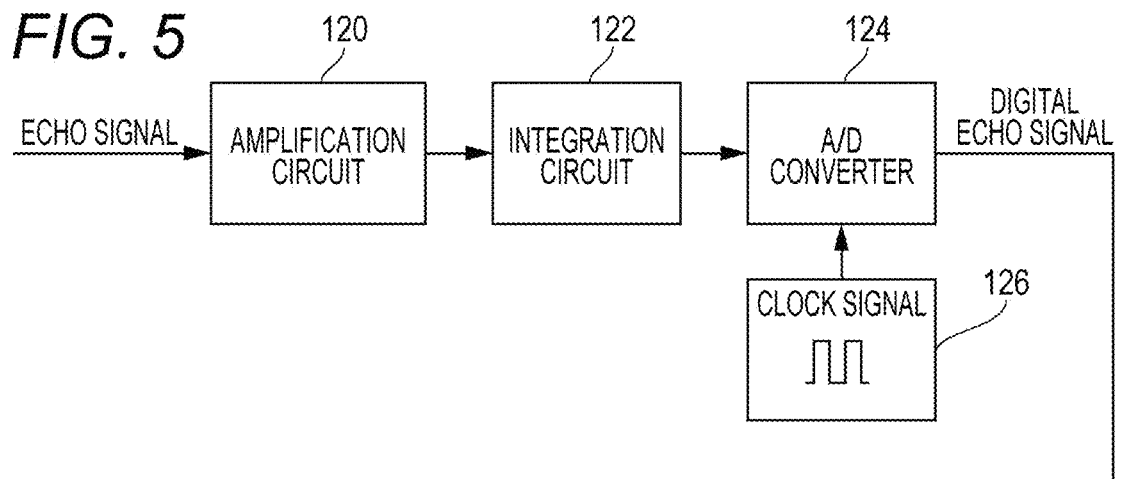
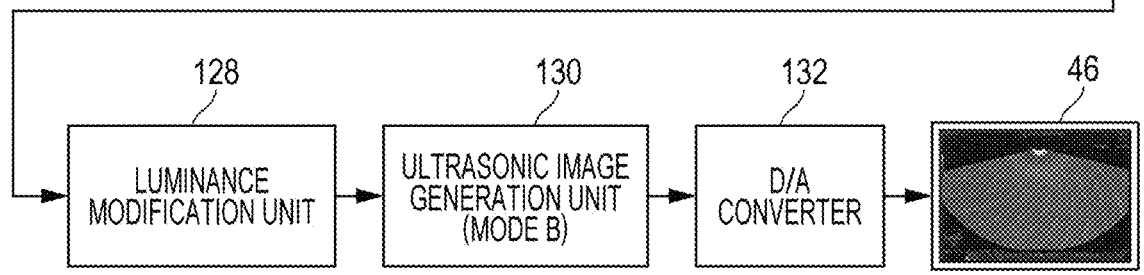
FIG. 6A
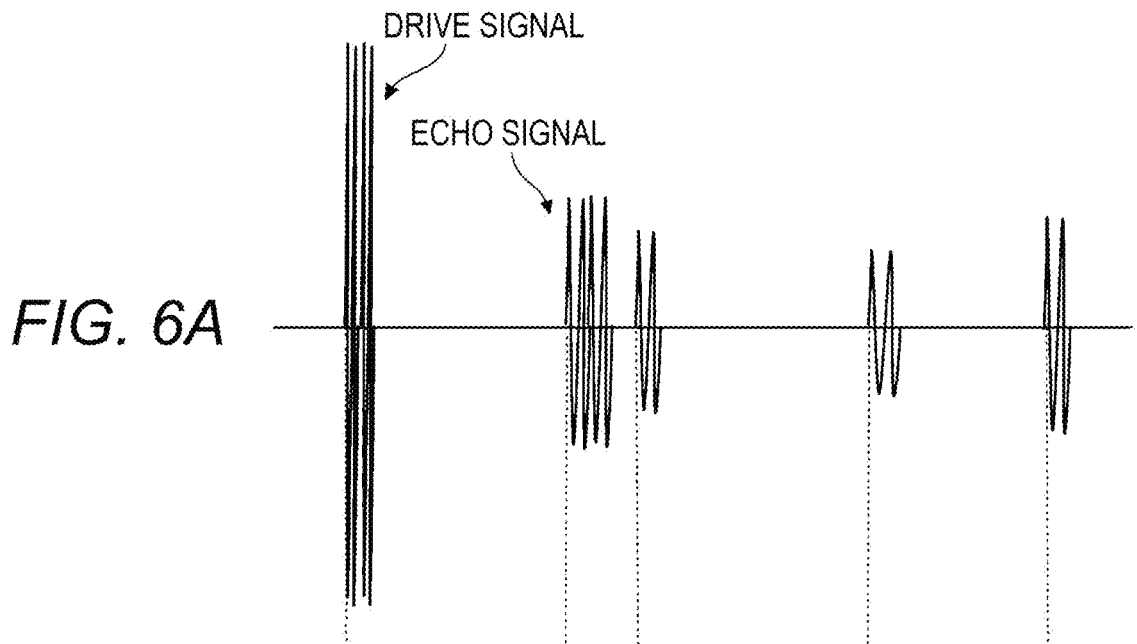
FIG. 6B
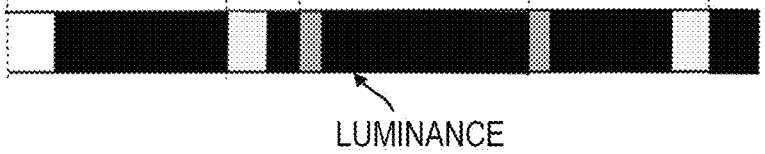

NOISE

ELECTRONIC ENDOSCOPE SYSTEM

TECHNICAL FIELD

The present invention relates to an electronic endoscope system that acquires an ultrasonic image.

BACKGROUND ART

An electronic endoscope system is used for observation and treatment of biological tissue inside a human body. In addition to acquiring an optical observation image of a subject by using an image sensor as an image of biological tissue, the electronic endoscope system is capable of obtaining an ultrasonic image (ultrasonic tomographic image) by using an ultrasonic endoscope which includes an ultrasonic probe. A processor connected to the ultrasonic endoscope functions as an ultrasonic diagnostic apparatus and performs inspection and diagnosis. Hereinafter, an endoscope that includes an image sensor and an ultrasonic probe is referred to as an ultrasonic endoscope (or an electronic endoscope).

An ultrasonic endoscope includes an image sensor and an ultrasonic probe. In a flexible pipe extending from the ultrasonic endoscope to a processor, an imaging signal transmission line is installed that connects the image sensor, which is provided at the distal tip of an insertion portion, to a connector which is connected to the processor. An imaging signal is transmitted through the imaging signal transmission line. Here, in the flexible pipe, an ultrasonic signal transmission line is installed that connects the ultrasonic probe, which is provided at the distal tip of the insertion portion, to the connector which is connected to the processor. An ultrasonic signal is transmitted through the ultrasonic signal line.

When inspection or diagnosis is performed using ultrasonic waves, power is supplied from the processor to the ultrasonic probe, and the ultrasonic probe transmits ultrasonic waves to the biological tissue and receives reflected waves. The reflected waves received by the ultrasonic probe are converted into an echo signal, and the echo signal is sent to the processor through the ultrasonic signal transmission line. Signal processing is performed by the processor to obtain an ultrasonic image.

The processor includes a switching power supply in addition to: a signal processing unit that performs data processing by using a transmission signal (ultrasonic signal, imaging signal) from the ultrasonic endoscope, and a control unit that controls an image display, and the like. The switching power supply generates and supplies a necessary voltage for operating each constituent device in the ultrasonic endoscope and the processor. The processor is connected to a monitor for displaying captured images and ultrasonic images.

In an ultrasonic image, which is obtained based on the echo signal of the ultrasonic probe and displayed on the monitor, noise generated in the ultrasonic endoscope or in the processor, or noise superimposed on the AC power supply and entering from outside is sometimes mixed as a noise component. The noise component includes, for example, a noise component caused by the switching of the switching power supply or a noise component caused by mutual interference between the transmission lines. For example, in the flexible pipe, because the imaging signal transmission line and the ultrasonic signal transmission line are provided close to each other, electrostatic coupling or electromagnetic coupling between the transmission lines becomes strong, and a pulse control signal or the like for controlling the image sensor interferes with the ultrasonic probe or the ultrasonic signal transmission line, thereby causing a noise component to be mixed with the echo signal.

Furthermore, the ultrasonic image sometimes also generates ultrasonic-specific noise called artifacts (virtual images that do not actually exist). An echo signal is obtained due to an ultrasonic wave being generated and an echo reflected from the inside of a living body being received. However, a virtual image, that is, an artifact is generated as noise due to factors such as side lobe artifacts, grating lobes, and multiple reflection. Further, when high-frequency noise generated by the switching power supply is superimposed on the reception signal of the ultrasonic signal, an artifact sometimes appear in the ultrasonic image generated in an ultrasonic diagnostic image.

Japanese Patent Laid-Open Application No. 2014 003801 discloses an ultrasonic image processor that is capable of removing periodic noise caused by the operation of the DC/DC converter from noise components in the ultrasonic image. The ultrasonic image processor includes a main converter that inputs power from a power input unit and outputs power of a constant voltage, and a plurality of sub-converters that inputs power of the constant voltage and outputs power to a circuit constituting the ultrasonic image processor, and switching operations of the main converter and the sub-converters are synchronized to reduce spike noise.

Japanese Patent Laid-Open Application No. 2019 076707 discloses a method of changing a switching frequency of a switching power supply by a preset change width in order to inhibit an increase in switching noise appearing on an ultrasonic image. This is because when the switching frequency becomes an integral multiple of a pulse repetition frequency, which is a frequency at which an ultrasonic pulse is transmitted when scanning is executed, switching noise caused by switching appears on an ultrasonic image which is based on ultrasonic image data generated by executing a mode B (Brightness) scan or a mode M (Motion) scan.

Japanese Patent Laid-Open Application No. 2017 080040 discloses a method in which an image generation unit, a detection unit, and a control unit are provided, and when the detection unit detects a peculiar change in output from an external device or an ultrasonic probe in a temporal direction, the control unit displays, on the display unit, a reference image including a medical image at substantially the same position as the ultrasonic image displayed on the display unit in response to the detection of the peculiar change by the detection unit, and removes noise.

SUMMARY OF INVENTION

Technical Problem

In an electronic endoscope system including an ultrasonic endoscope and a processor, it is preferable to accurately extract and image an echo signal that is likely to be buried in a noise component, in order to achieve a more accurate diagnosis. Furthermore, in order to reduce the physical burden on a patient into whose body cavity the ultrasonic endoscope is inserted, further reduction in the diameter of the flexible pipe will be required in the future. In an ultrasonic signal transmission line and an imaging signal transmission line in which the invasion of noise is inhibited using a conventional transmission line shield structure, the shielding performance inevitably deteriorates due to the restriction of the shield structure caused by the reduction in diameter, and thus a noise component is easily generated.

Furthermore, in a case where noise is superimposed from the outside on an AC power supply that is a power source for driving the ultrasonic endoscope and the processor, the noise is reduced to some extent by a power supply circuit or a filter circuit. However, in a case where the noise level is significant or in a case where EMI noise or the like is superimposed on an echo signal by an unintended route, the noise becomes a noise component of the ultrasonic image, leading to a reduction in image quality. Moreover, detection of a minute echo signal is also required to attain high definition, and how to inhibit a noise component in an ultrasonic image is a major problem.

An object of the present invention is to provide an electronic endoscope system that, when an ultrasonic image is acquired using an ultrasonic probe, is capable of efficiently detecting a noise component which is periodically generated in the ultrasonic image, inhibiting the noise component, and generating a high-quality ultrasonic image.

Solution to Problem

One aspect of the present invention is an electronic endoscope system that acquires an ultrasonic image, the electronic endoscope system including:

an electronic endoscope having, at a distal tip thereof, an ultrasonic probe that repeatedly applies ultrasonic waves to biological tissue to sequentially obtain echo signals; and an ultrasonic image processor that has an ultrasonic image processing unit that processes the echo signals outputted from the ultrasonic probe to generate an ultrasonic image, a noise detection unit that detects a noise component which is contained in a first echo signal among the echo signals and which is periodically generated at or above a preset threshold level, and a noise inhibition unit that generates a noise inhibition component which, by being added to a second echo signal outputted after the first echo signal, inhibits generation of the noise component in the second echo signal, and that adds the noise inhibition component to the second echo signal.

The noise inhibition component is preferably a component having an opposite phase to that of the noise component.

The noise inhibition unit preferably includes a noise inhibition component correction unit that adjusts at least any one of an amplitude, a frequency, and a phase of the noise inhibition component so that the level of the noise component is reduced in the second echo signal to which the noise inhibition component is added.

The noise detection unit preferably further detects the noise component contained in the second echo signal to which the noise inhibition component has been added.

The electronic endoscope system preferably further includes a display unit that is configured to display the ultrasonic image on a display screen, in which, when the noise component is detected in the second echo signal to which the noise inhibition component has been added, the display unit causes the display screen to render a display prompting inhibition of the noise component.

The noise detection unit preferably includes a period width detection unit that calculates a noise generation period in which the noise component is periodically generated and calculates a period width from a minimum value and a maximum value of the noise generation period, in which the noise detection unit preferably detects the noise component by using the noise generation period and the period width.

The noise detection unit creates a noise component inference model in which the presence or absence of the noise component is machine-learned in advance by using, as training data, a training ultrasonic image without the noise component and a training ultrasonic image having the noise component, and determines the presence or absence of the noise component by inputting the ultrasonic image generated by the ultrasonic image processing unit to the noise component inference model.

Another aspect of the present invention is an electronic endoscope system that acquires an ultrasonic image, the electronic endoscope system including:

an electronic endoscope having, at a distal tip thereof, an ultrasonic probe that repeatedly applies ultrasonic waves to biological tissue to sequentially obtain echo signals; and an ultrasonic image processor that has an ultrasonic image processing unit that processes the echo signals outputted from the ultrasonic probe to generate an ultrasonic image.

Either one of the electronic endoscope and the ultrasonic image processor includes:

a noise detection unit that detects an external noise component that is superimposed on a cable transmitting the echo signals outputted from the ultrasonic probe; and a noise inhibition unit that generates a noise inhibition component which inhibits the external noise component, and that applies the noise inhibition component to the cable.

The noise inhibition component may be a component having an opposite phase to that of the external noise component.

Either the electronic endoscope or the ultrasonic image processor may include an antenna that acquires the external noise component from the cable.

Advantageous Effects of Invention

With the electronic endoscope system described above, when an ultrasonic image is acquired using an ultrasonic probe, it is possible to efficiently detect a noise component which is periodically generated in the ultrasonic image, inhibit the noise component, and generate a high-quality ultrasonic image.

BRIEF DESCRIPTION OF DRAWINGS

FIG. 5 is a diagram illustrating an example of signal processing up until an echo signal during acquisition of an ultrasonic image is displayed as a mode-B ultrasonic image.

FIGS. 6A and 6B are diagrams illustrating an example of an echo signal after the echo signal in mode A illustrated in FIG. 4A passes through an amplification circuit and an integration circuit, and an example of luminance-modulated brightness.

DESCRIPTION OF EMBODIMENTS (Overall Configuration of Electronic Endoscope System)

Figure 1:
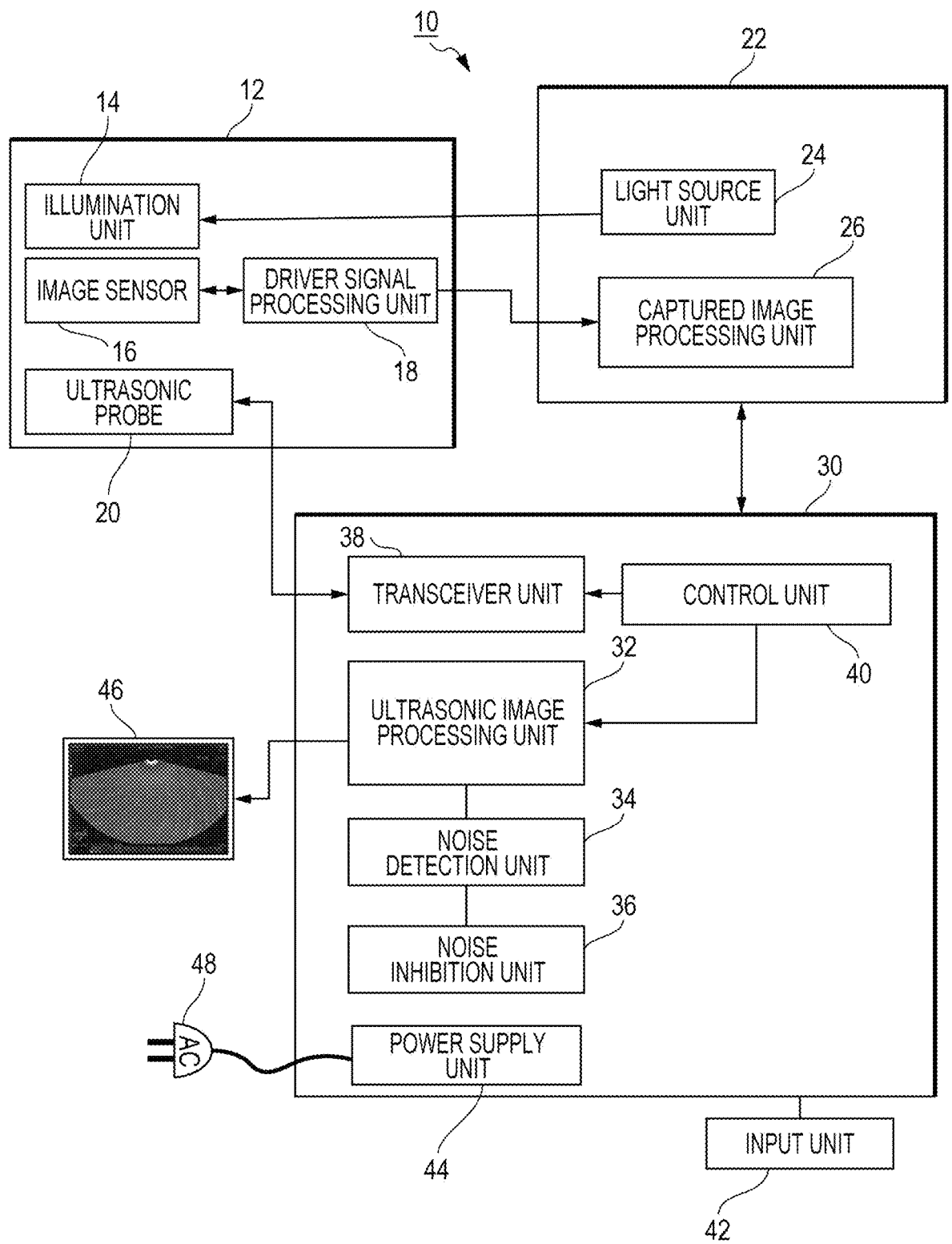
FIG. 1 is a block diagram illustrating an example of the overall configuration of an electronic endoscope system according to a first embodiment.

FIG. 1 is a block diagram illustrating an example of the overall configuration of an electronic endoscope system according to a first embodiment. An electronic endoscope system 10 that acquires an ultrasonic image includes an electronic endoscope 12, a captured image processor 22, and an ultrasonic image processor 30.

The electronic endoscope 12 includes an illumination unit 14 that irradiates biological tissue, an image sensor 16 that images the biological tissue, a driver signal processing unit 18 that preprocesses a signal captured by the image sensor 16, and an ultrasonic probe 20 that applies ultrasonic waves to the biological tissue to obtain an echo signal. The ultrasonic probe 20 is a phased array-type probe that is capable of acquiring an echo signal along various directions due to each probe element, in which a plurality of probe elements which output ultrasonic waves are arranged in a predetermined direction, outputting ultrasonic waves with a predetermined time difference. The ultrasonic probe 20 repeatedly applies such ultrasonic waves to sequentially obtain echo signals.

The image signal of the biological tissue is inputted from the image sensor 16 to the driver signal processing unit 18 in predetermined frame periods, and is outputted to the system controller 102 and a captured image processing unit 26 of the captured image processor 22. The frame periods are $\frac{1}{30}$ second, $\frac{1}{60}$ second, for example.

The driver signal processing unit 18 also accesses a memory 92 and reads device-specific information of the electronic endoscope 12. The device-specific information of the electronic endoscope 12 recorded in the memory 92 includes, for example, the number of pixels or sensitivity of the image sensor 16, an operable frame rate, a model number, and the like.

The captured image processor 22 includes a light source unit 24 that transmits a light source to the illumination unit 14, and a captured image processing unit 26 that generates a captured image by processing an imaging signal that is outputted from the image sensor 16.

The ultrasonic image processor 30 includes a transceiver 38 that transmits a drive signal to the ultrasonic probe 20 and receives echo waves; an ultrasonic image processing unit 32 that processes an echo signal from the ultrasonic probe 20 and generates an ultrasonic image; a noise detection unit 34 that detects a noise component which is contained in the echo signal (a first echo signal) and that is periodically generated at or above a preset threshold level; and a noise inhibition unit 36 that generates a noise inhibition component which, by being added to an echo signal (second echo signal) outputted subsequently, inhibits the detected noise component in the echo signal, and that adds the noise inhibition component to the echo signal.

Based on the digital echo signal, the ultrasonic image processing unit 32 performs predetermined computation as grayscale image data by, for example, luminance modification, and generates a one-dimensional mode-B image along one direction. Furthermore, the ultrasonic image processing unit 32 creates one two-dimensional mode-B image by arranging, along a predetermined azimuth direction in accordance with phased array scanning, a one-dimensional mode-B image along a plurality of directions generated based on an echo signal which is obtained from a phased array-type ultrasonic probe 20. Further, image processing using known techniques such as gain processing and contrast processing is performed on the created image, and shade processing corresponding to the image display range of an ultrasonic image display unit 46 is performed.

The ultrasonic image processor 30 includes a display unit 46 that has a display for a generated ultrasonic image and an input function that enables inputs using a touch-panel system. The ultrasonic image processor 30 further includes an input unit 42 that operates the ultrasonic image processor 30, a power supply unit 44, and an AC power input unit 48.

The input unit 42 receives inputs of various types of information by using a keyboard, a mouse, a touch panel, or the like. The ultrasonic image display unit 46 displays various types of information including the generated ultrasonic image. The power supply unit 44 supplies power for driving the electronic endoscope 12 and the captured image processor 22 in addition to the ultrasonic image processor 30. The power supply unit 44 includes, as a constituent device, a DC/DC converter constituting a switching power supply, for example, and generates a DC voltage using the switching frequency of the DC/DC converter. A plurality of DC/DC converters are provided, and each DC/DC converter converts an input DC voltage into a desired DC voltage and supplies power to each device.

The noise detection unit 34 detects whether or not the echo signal (first echo signal) among the received echo signals includes a noise component which is periodically generated at or above a preset threshold level. There are no particular limitations on the method for detecting the noise component. However, it is preferable, for example, to provide a period width detection unit (a unit for extraction of amplitude and the like) to be described subsequently) that calculates a noise generation period in which the noise component is periodically generated and that calculates a period width from a minimum value and a maximum value of the noise generation period. The noise detection unit preferably detects the noise component by using the noise generation period and the period width.

The noise detection unit 34 may further perform frequency analysis utilizing a fast Fourier transform (FFT) to determine whether or not there is a spectrum peak at or above the set threshold level. Because the echo signal reflected at the boundary surface of the biological tissue does not have periodicity, a spectral peak rarely exists, and hence a spectral peak is likely to be a peak of a periodically generated noise component.

The noise inhibition component is a component added to an echo signal (second echo signal) which is subsequently outputted from the ultrasonic probe 20 such that the generation of the detected noise component is inhibited. The noise inhibition component will be described subsequently.

Electronic Endoscope

Figure 2:
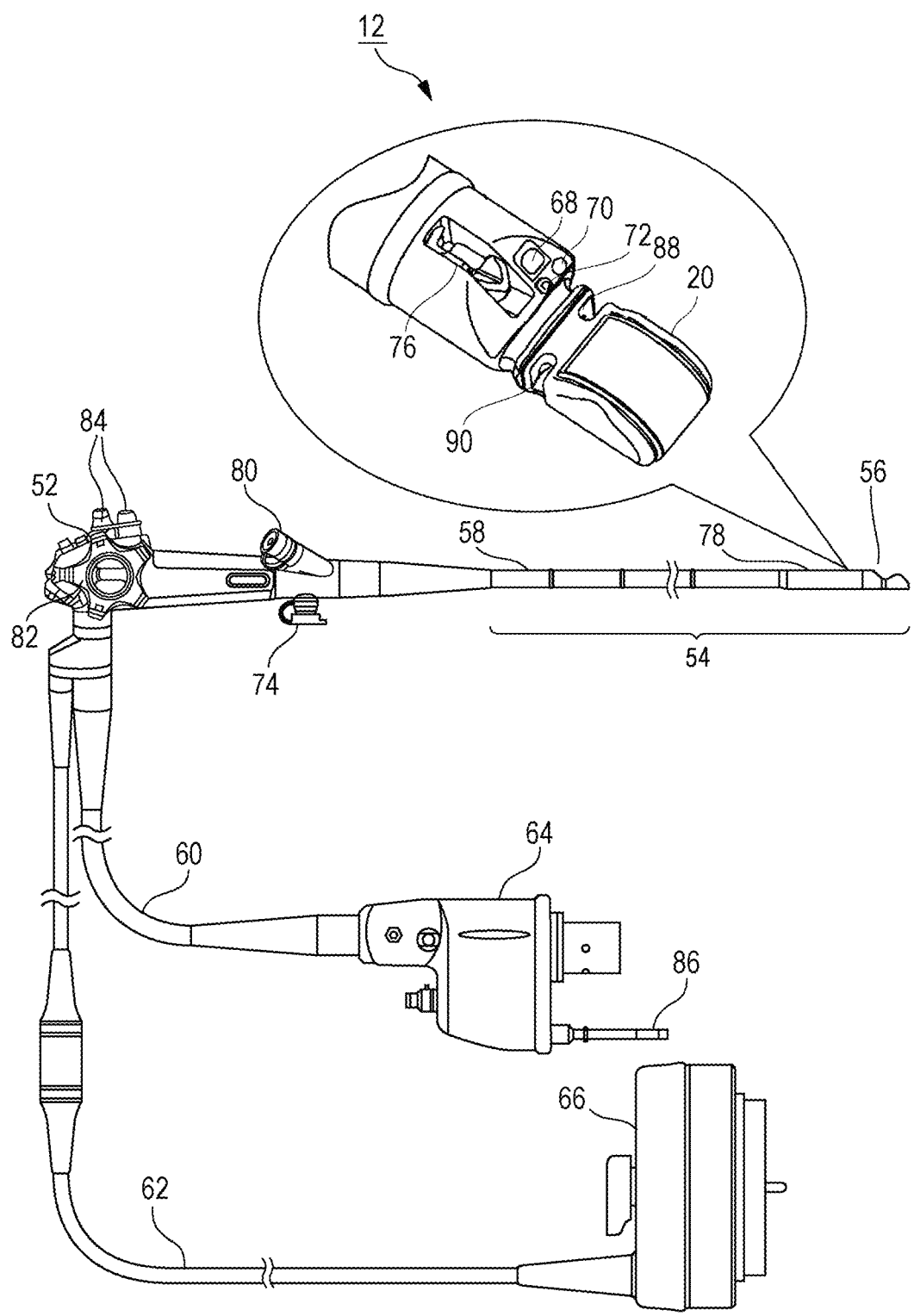
FIG. 2 is a diagram illustrating an example of an electronic endoscope that includes an ultrasonic probe which is used in the electronic endoscope system according to the first embodiment.

FIG. 2 is a diagram illustrating an example of an electronic endoscope that includes an ultrasonic probe which is used in the electronic endoscope system according to the first embodiment.

The electronic endoscope 12 includes an operation unit 52, an insertion portion 54 which includes a distal tip 56 and a mainly internal soft portion 58, a flexible cable 60 which has a light guide cable therein, a scanner connector cable 62, a connector 64, and a scanner connector 66.

The distal tip 56 is a sensor that inspects biological tissue, and includes an image sensor unit 68, an emission end surface 70, and an ultrasonic probe 20. The ultrasonic probe 20 has a transducer array in which a plurality of ultrasonic transducers, for example, piezoelectric elements are arrayed as probe elements. Each of these transducers transmits ultrasonic waves according to a drive signal, receives reflected waves from the subject, and outputs an analog reception signal. Each of the transducers is configured using, for example, an element in which electrodes are formed at both ends of a piezoelectric body made of lead zirconate titanate (PZT) which is a piezoelectric ceramic, or polyvinylidene difluoride (PVDF) which is a polymer piezoelectric element.

In the image sensor unit 68 of the distal tip 56, the image sensor unit 68 is provided with the image sensor 16, and an objective lens, an illumination lens, and the like (not illustrated) for imaging using the image sensor 16. The objective lens forms an image of return light from the biological tissue, which has been irradiated with the illumination light, on the light receiving surface of the image sensor 16. The image sensor 16 is, for example, a single-plate color charge-coupled device (CCD) image sensor having a Bayer pixel arrangement. The single-plate color CCD image sensor accumulates the optical image formed by each pixel on the light receiving surface as electrical charge corresponding to the amount of light, and generates and outputs an image signal corresponding to the color components of red (R), green (G), and blue (B). The image sensor 16 is not limited to a CCD image sensor, rather, a complementary metal oxide semiconductor (CMOS) image sensor or another type of imaging device can also be used. The image sensor 16 may incorporate a complementary color filter.

Figure 3:
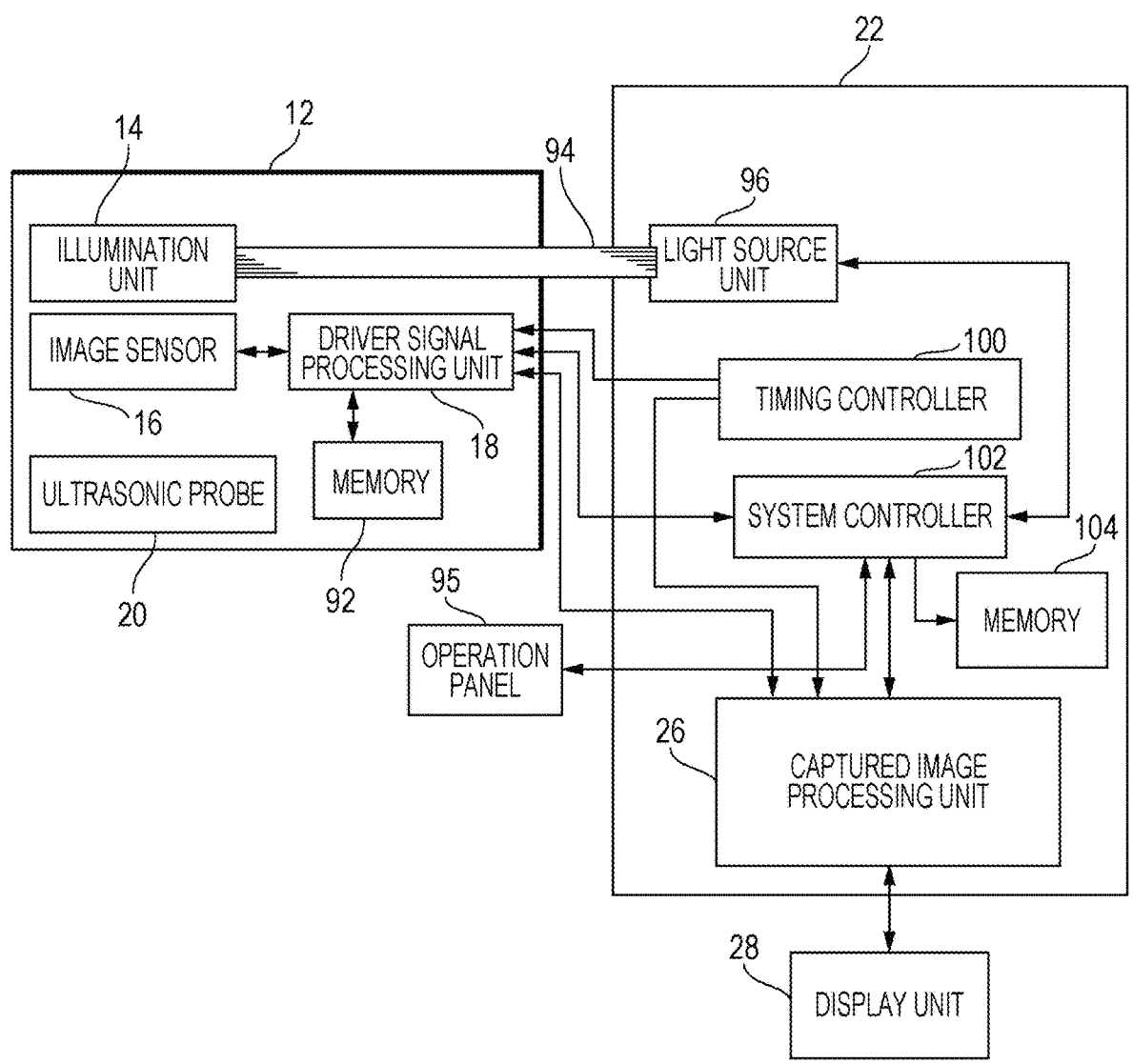
FIG. 3 is a block diagram illustrating an example of a schematic configuration of an electronic endoscope and a captured image processor which are used in an electronic endoscope system according to the first embodiment.

The incident illumination light is emitted, through the light distribution lens, from the emission end surface 70 at the distal tip 56. The illumination light enters the illumination unit 14 of the electronic endoscope 12 via a light guide 94 (FIG. 3).

The outer portion of the distal tip 56 is made of a hard resin.

The distal tip 56 further includes an air/water supply nozzle 72 that discharges or sucks liquid or gas. The air/water supply nozzle 72 discharges liquid such as water for cleaning the surfaces of the objective lens and the illumination lens associated with the image sensor 16, and discharges gas such as air for removing liquid or foreign matter that remains on the surfaces of the objective lens and the illumination lens. Here, a balloon (not illustrated) used for performing ultrasonic diagnosis by being filled with a liquid and bringing the liquid into contact with biological tissue is attached to the distal tip 56, and a balloon water injection port 88 and a balloon water suction port 90 are provided. Furthermore, the distal tip 56 is provided with a forceps elevator 76 for bringing a flexible puncture needle (not illustrated) into contact with biological tissue, and is also provided with an opening for sucking liquid or gas on the biological tissue via a forceps elevator 76.

The insertion portion 54 is provided with a bending section 78 that bends in the vertical direction and the horizontal direction. A portion on the proximal end side (the operation unit 52 side) with respect to the bending section 78 is a flexible soft portion 58 that can be bent under its own weight or according to an operation by the practitioner.

The soft portion 58 is provided between the bending section 78 and the operation unit 52, and is provided therein with a signal line of a sensor provided at the distal tip 56 and with a plurality of individual channels through which gas or fluid flows from the aforementioned opening. These individual channels are formed by pipes, tubes, or long holes.

On the side of the distal tip 56 of the operation unit 52, a flexible treatment tool insertion port protrusion 80 for inserting a puncture needle and a forceps raising wire cleaning port 74 are provided in a protruding manner. A cap is detachably attached to an end opening of the treatment tool insertion port protrusion 80. A treatment tool insertion/suction pipe that extends from the treatment tool insertion port protrusion 80 toward the distal tip 56 and that is flexible is provided inside the insertion portion 54. The treatment tool insertion/suction pipe is opened by the forceps elevator 76. The puncture needle inserted into the treatment tool insertion/suction pipe from the treatment tool insertion port protrusion 80 can protrude outward from the distal tip opening of the treatment tool insertion/suction pipe in the forceps elevator 76, and is used to palpate the biological tissue by protruding from the distal tip opening.

The operation unit 52 includes a plurality of operation buttons 84 of a channel switching switch, and a common channel through which a fluid flows and which extends from the connector 64 and within the flexible cable 60, is provided in the operation unit. A bending operation lever 82 is a lever operated by the practitioner to bend the bending section 78 in the vertical direction and the horizontal direction. The bending section 78 is bent in the vertical direction and the horizontal direction according to the rotation operation of the bending operation lever 82.

The flexible cable 60 connects the connector 64, which is connected to the captured image processor 22, and the operation unit 52. The connector 64 is also provided with an opening port of a common channel for supplying or sucking fluid.

The connector 64 includes a light source insertion portion 86 and is connected to the captured image processor 22. The illumination light generated by the light source unit in the captured image processor 22 is transmitted from the connector 64 toward the distal tip 56 through the flexible cable 60, the operation unit 52, and the light guide cable in the insertion portion 54. Furthermore, from the connector 64, a drive signal is sent from the captured image processor 22 to the image sensor 16 via a signal line in the flexible cable 60. The image signal captured by the image sensor 16 is sent to the captured image processor 22 via the flexible cable 60, the operation unit 52, and the signal line in the insertion portion 54.

The scanner connector 66 is connected to the ultrasonic image processor 30, and transmits an echo signal scanned by the ultrasonic probe 20 to the ultrasonic image processing unit 32 via the scanner connector cable 62. The ultrasonic image processing unit 32 processes the echo signal to generate a diagnostic image of the biological tissue to be examined, and displays the generated image on the display unit 46. Further, the scanner connector cable 62 transmits the drive signal of the ultrasonic probe 20 from the ultrasonic image processor 30 to the piezoelectric element of the ultrasonic probe 20. The piezoelectric element is capable of converting electrical energy into mechanical energy, and generates ultrasonic waves through expansion and contraction due to voltage changes.

The connector 64 is connected to the driver signal processing unit 18. An image signal of the biological tissue is inputted from the image sensor 16 to the driver signal processing unit 18 in predetermined frame periods, and is outputted to the system controller and the captured image processing unit 26 of the captured image processor 22. The frame periods are 1/30 second, 1/60 second, for example.

Processor for an Endoscope

FIG. 3 is a block diagram illustrating an example of a schematic configuration of an electronic endoscope and a captured image processor which are used in the electronic endoscope system according to the first embodiment. The captured image processor 22 includes a system controller 102 and a timing controller 100 for control purposes. The system controller 102 executes various programs stored in the memory 104 and integrally controls the entire electronic endoscope system 10. The system controller 102 is connected to an operation panel 95.

The system controller 102 changes each operation of the electronic endoscope system 10 and the parameters for each operation according to instructions from the operator, which are inputted via the operation panel 95. Input instructions by the operator include a switching instruction, or the like, to switch the operation mode of the electronic endoscope system 10. According to the first embodiment, a normal mode and a special mode exist as operation modes. The timing controller 100 outputs a clock pulse for adjusting the timing of the operation of each unit to each component in the electronic endoscope system 10.

A light source unit 96 transmits illumination light to the illumination unit 14 of the electronic endoscope 12 through the light guide 94. As the light source, for example, a high brightness lamp such as a xenon lamp, a halogen lamp, a mercury lamp, or a metal halide lamp is used. The illumination light transmitted from the light source is condensed by a condenser lens (not illustrated), and is limited to an appropriate light amount via an aperture. A motor is mechanically connected to the aperture via a transmission mechanism such as an arm or a gear (not illustrated). The aperture can have its degree of opening changed in order to set a video displayed on the display screen of the captured image display unit 28 at an appropriate brightness.

The illumination light that has passed through the aperture falls incident on the illumination unit 14 of the electronic endoscope 12 via the light guide 94. The incident illumination light passes through the light distribution lens and is emitted from the emission end surface 70 at the distal tip 56.

As the light source of the light source unit 96, instead of a white light source that emits white light, a semiconductor light emitting element such as a light emitting diode or a laser diode that emits light in a predetermined wavelength region may be used.

The system controller 102 performs various calculations on the basis of the device-specific information of the electronic endoscope 12 and generates a control signal. The system controller 102 uses the generated control signal to control the operation and timing of various circuits in the captured image processor 22 so as to perform processing suitable for the electronic endoscope 12 connected to the captured image processor 22. The system controller 102 acquires the device-specific information of the memory 92 that is read out by the driver signal processing unit 18.

The timing controller 100 supplies the clock pulse to the driver signal processing unit 18 in accordance with timing control by the system controller 102. The driver signal processing unit 18 performs driving control on the image sensor 16 using timing that is synchronized with the frame rate of video being processed on the captured image processor 22 side, in accordance with the clock pulse supplied by the timing controller 100.

The captured image processor 22 includes the captured image processing unit 26. The captured image processing unit 26 exhibits its functions due to the system controller 102 reading out and executing the programs recorded in the memory 104. Thus, because the captured image processing unit 26 functions integrally with the system controller 102, the former may be provided inside the system controller 102.

The captured image processing unit 26 is provided with a pre-stage signal processing circuit, and performs demosaic processing on each of R, G, and B image signals inputted from the driver signal processing unit 18 in a frame period. Specifically, interpolation processing using peripheral pixels G and B is performed on each R image signal, interpolation processing using peripheral pixels R and B is performed on each G image signal, and interpolation processing using peripheral pixels R and G is performed on each B image signal. As a result, all the image signals are converted into image data having information of the three color components R, G, and B. Further, the pre-stage signal processing circuit performs known processing such as color correction, matrix calculation, and white balance correction.

The captured image processing unit 26 may include a post-stage signal processing circuit. The post-stage signal processing circuit performs predetermined signal processing on the image data to generate moving image data, and converts the moving image data into a predetermined video format signal. The converted video format signal is used to display a moving image on the display unit 28. Thus, a moving image of biological tissue is displayed on the display screen.

Imaging Mode of Ultrasonic Image Processor

The imaging modes of the ultrasonic image processor 30 include at least a mode A and a mode B. Mode A is a mode for displaying, on the time axis, amplitude information of an echo signal of a predetermined direction in the subject. Mode B is a mode for generating and displaying a one-dimensional image or a two-dimensional image along a predetermined direction representing the shape of the tissue in the subject.

Figure 4:
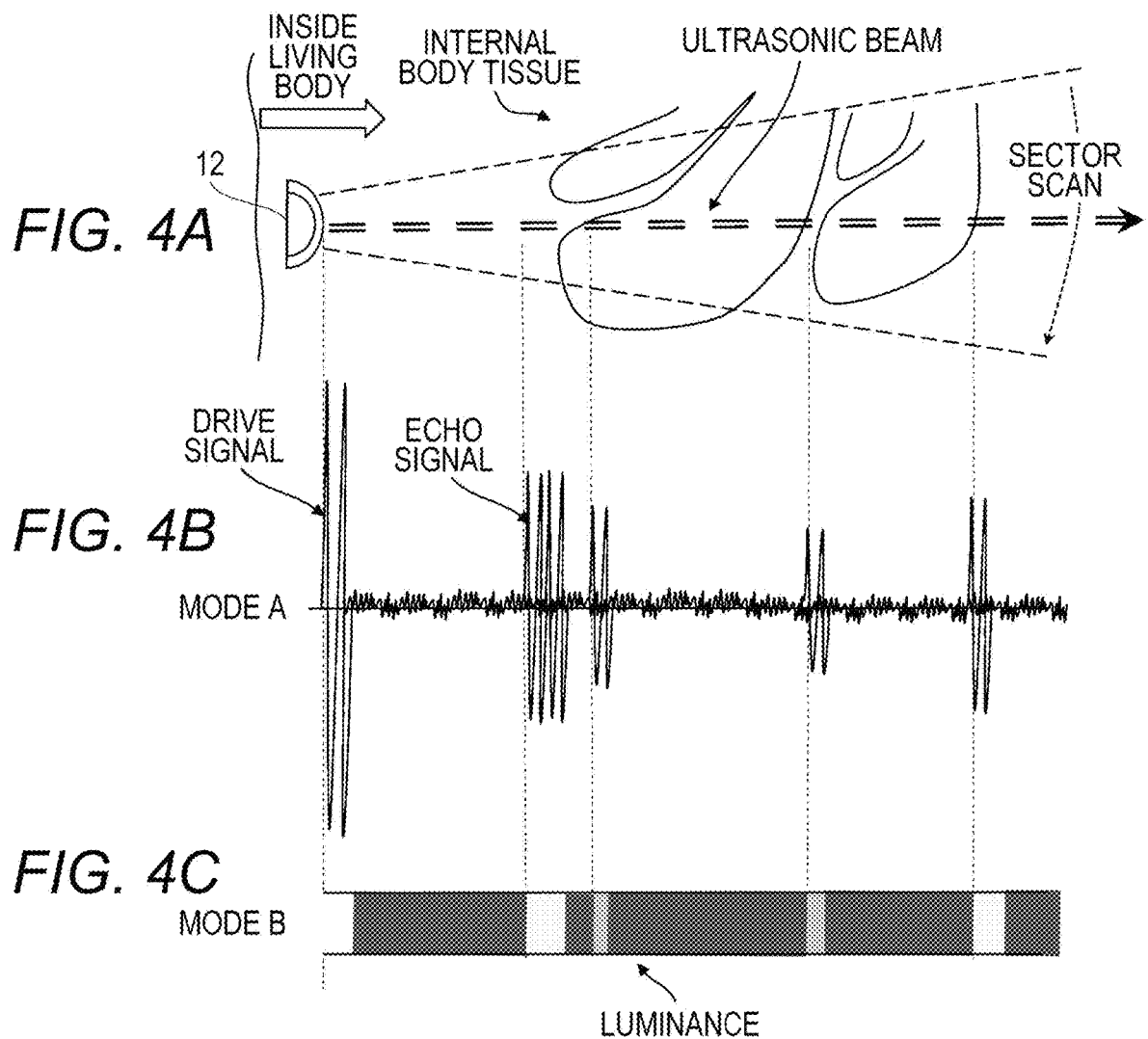
FIGS. 4A to 4C are diagrams illustrating an image forming principle for an ultrasonic image in the electronic endoscope system according to the first embodiment.

FIGS. 4A to 4C are diagrams illustrating an image forming principle for an ultrasonic image in the electronic endoscope system according to the first embodiment. Image formation using ultrasonic waves is based on the ultrasonic pulse reflection method. FIG. 4A illustrates a state in which an ultrasonic beam is generated from the ultrasonic probe 20 in the living body. The ultrasonic beam emits, for example, ultrasonic waves of around 10 MHz in the form of a pulse into the living body from the ultrasonic probe 20. The emitted ultrasonic waves become reflected waves due to the difference in acoustic impedance of the biological tissue within the living body, and are received once again by the ultrasonic probe 20. This reflected wave becomes an echo signal.

The scanning of the ultrasonic beam by the electronic endoscope 12 is sector scanning using the phased array method, and an echo signal along a predetermined direction can be obtained using the sector scanning. FIG. 4B illustrates an example of an echo signal using a mode A display. In mode A, the horizontal axis represents time, and the vertical axis represents the reflection intensity (amplitude), and an echo signal is displayed. Time represents the depth of the living body, and is a distance between one internal body tissue and the next internal body tissue.

As illustrated in FIG. 4C, mode B involves subjecting the waveform of a mode-A echo signal to luminance conversion by modulating the luminance according to the reflection intensity, and using the luminance to represent a tomographic image as a grayscale image. The imaging mode of the ultrasonic image processor 30 may further include a known mode M and a Doppler mode.

FIG. 5 is a diagram illustrating an example of conventionally used signal processing up until an echo signal during acquisition of an ultrasonic image is displayed as a mode-B ultrasonic image. The echo signal obtained by the ultrasonic probe 20 is amplified by the amplification circuit 120 and integrated by the integration circuit 122 to remove harmonic noise. The amplification circuit 120 and the integration circuit 122 may include an amplification function and a low-pass filter function due to an integrated inverting amplification-type integration circuit. Next, the echo signal, which is an analog signal, is digitized by the A/D converter 124 in a sampling period using the clock signal 126, thus becoming a digital echo signal.

The digital echo signal is converted to luminance due to a luminance modification unit 128 modulating the luminance according to the reflection intensity. The digital echo signal thus converted into luminance is subjected to image processing in the ultrasonic image generation unit 130 and becomes a two-dimensional mode-B tomographic image. This digital image signal is converted into an analog signal by the D/A converter 132, and is displayed as a mode-B tomographic image by the ultrasonic image display unit 46.

FIGS. 6A and 6B are diagrams illustrating an example of an echo signal and a luminance signal after the mode-A echo signal illustrated in FIG. 4A passes through the amplification circuit 120 and the integration circuit 122. As illustrated in FIG. 6A, high-frequency noise is removed from the mode-A echo signal illustrated in FIG. 4A. As illustrated in FIG. 6B, the mode-A echo signal is a luminance signal from which high-frequency noise has been removed. Thus, conventional ultrasonic-image noise processing is basically performed by the amplification circuit 120 and the integration circuit 122 illustrated in FIG. 5, or by an inverting amplification circuit in which the amplification circuit and the integration circuit are integrated. Note that a frequency of ½ or more of the sampling frequency using the clock signal 126 of the A/D converter 124 is a frequency that is not digitized by sampling, and the A/D converter 124 also serves as one type of low-pass filter.

Periodically Generated Noise Component

Figure 7:
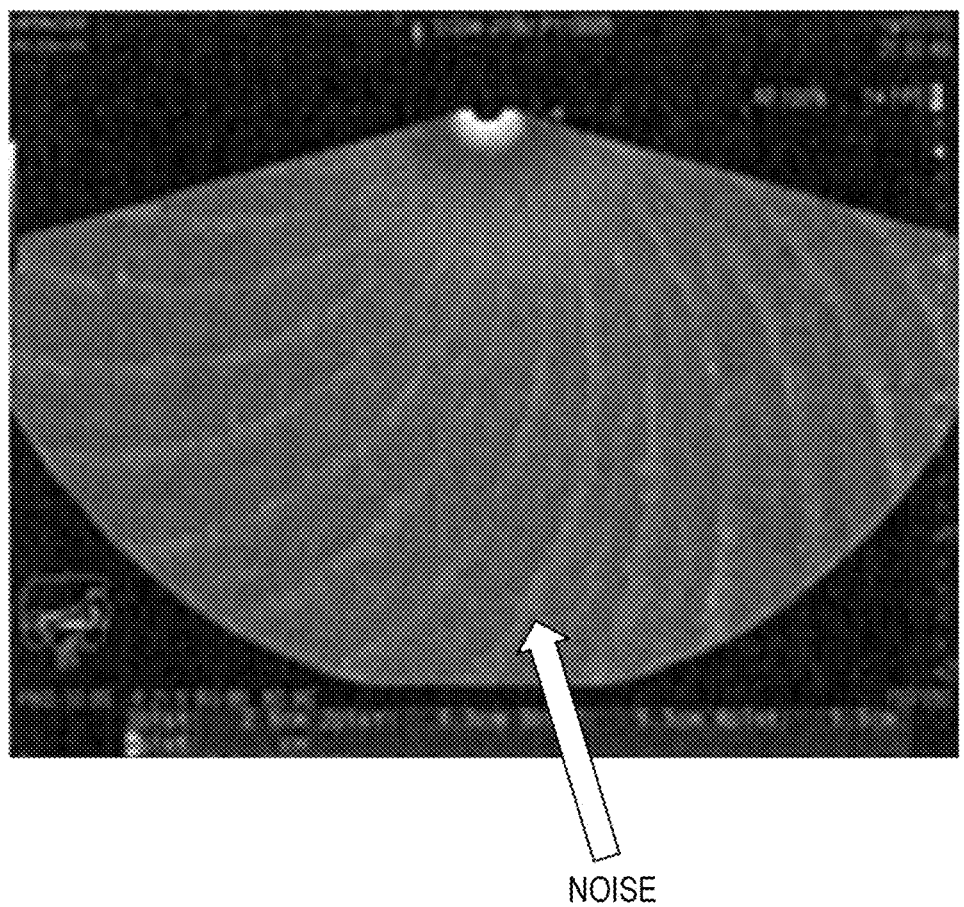
FIG. 7 is a diagram illustrating an example of a mode-B ultrasonic image obtained by the electronic endoscope system according to the first embodiment.

FIG. 7 is a diagram illustrating an example of a mode-B ultrasonic image obtained by the electronic endoscope system according to the first embodiment. A fan-shaped portion obtained by sector scanning is an ultrasonic image, and an upper white portion corresponds to a drive signal of the ultrasonic probe 20. In this example, as indicated by the arrow, a bent white curve that extends radially appears, and constitutes a noise component having a period (strictly speaking, a period varying within a certain range).

Figure 8:
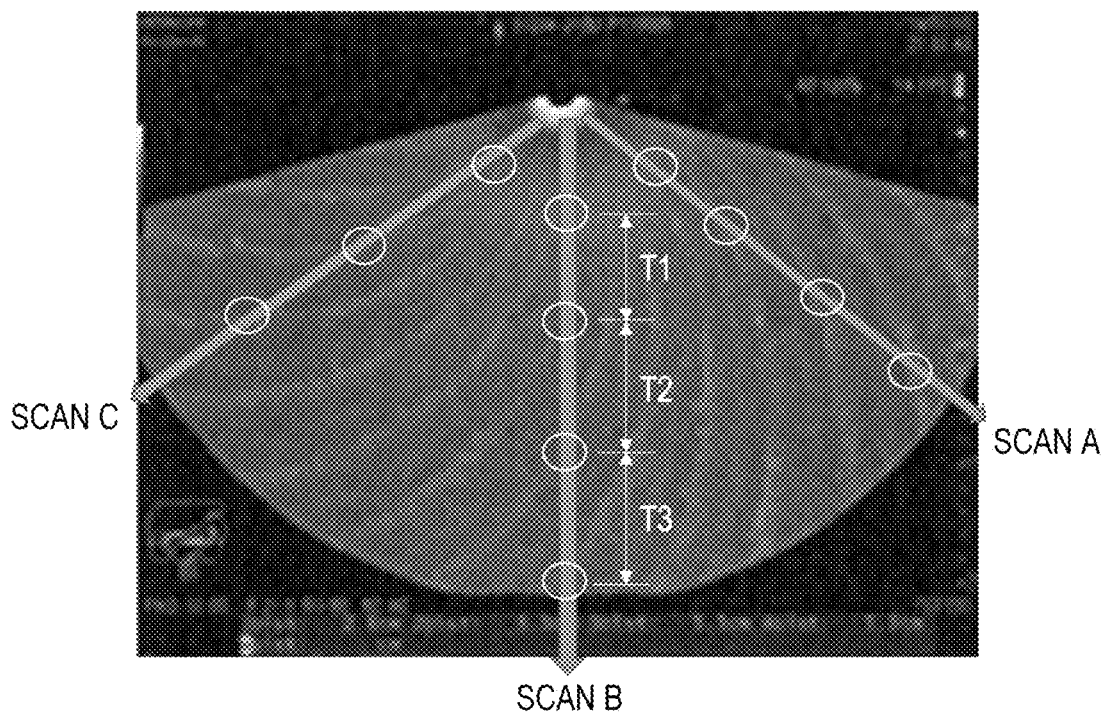
FIG. 8 is a diagram illustrating an example of a scan position of an ultrasonic beam in the mode-B ultrasonic image obtained by the electronic endoscope system according to the first embodiment, and a noise component generation unit.

FIG. 8 is a diagram illustrating an example of a scan position of an ultrasonic beam in the mode-B ultrasonic image obtained by the electronic endoscope system according to the first embodiment, and a noise component generation unit. Portions where noise is generated in scan A, scan B, and scan C, which have different scan positions, are indicated by circle marks. For example, the noise is generated in four positions in scan B, and assuming that the time intervals are T1, T2, and T3, time intervals T1, T2, and T3 are generated with certain widths. The time intervals T1, T2, and T3 are not constant, and are time intervals within a certain range.

Furthermore, it can be seen that, similarly to scan B, the time intervals of noise generation in scan A and scan C are not constant and occur in time intervals within a certain range. Therefore, noise components that appear as radial bent curves have, in a scan, period widths within a certain range. That is, same are considered to be periodic noise components that are periodically generated in a certain frequency band in the frequency domain.

Figure 9:
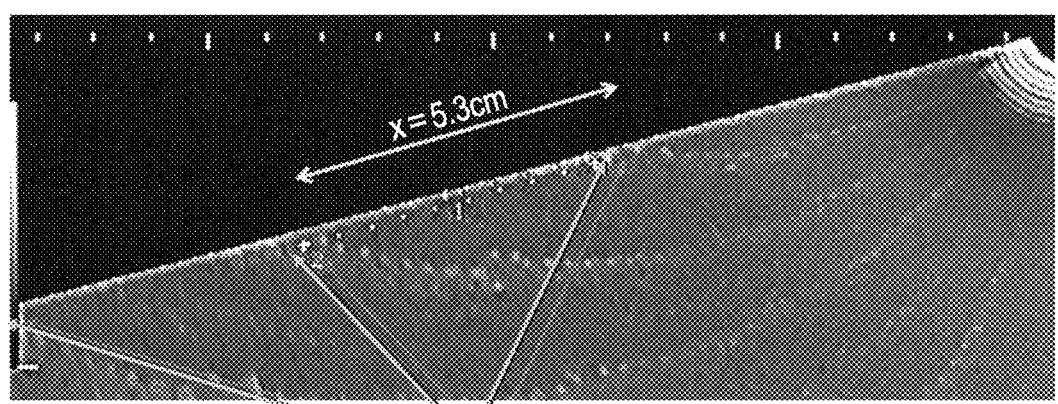
FIG. 9 is a diagram illustrating an example of a generation frequency of a noise component appearing in the mode-B ultrasonic image obtained by the electronic endoscope system according to the first embodiment.

FIG. 9 is a diagram illustrating an example of a generation frequency of a noise component appearing in the mode-B ultrasonic image obtained by the electronic endoscope system according to the first embodiment. When the interval x between the high brightness points representing the noise component is measured, 5.3 cm is obtained. Assuming that the sound velocity in the living body is v, the noise generation frequency fn can be expressed by fn=v/2x. Assuming that the sound velocity v is, for example, 1540 m/s, the generation frequency fn of the noise component is 14.5 kHz. This frequency becomes a pass band of a frequency characteristic of the low-pass filter in the integration circuit 122 or the inverting amplification-type integration circuit, and cannot be handled by conventional noise processing. Note that the sound velocity depends on the biological tissue, and is, for example, 1570 m/s for blood, 1450 m/s for fat, 1560 m/s for the kidney, and 1590 m/s for muscle. The average is 1540 m/s.

Figure 10:
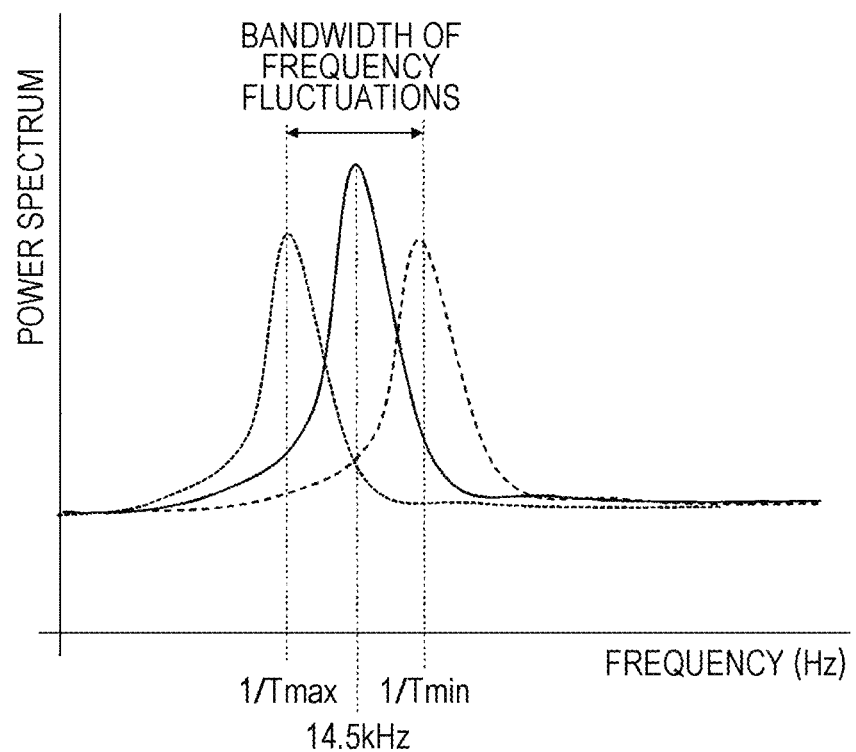
FIG. 10 is a diagram schematically illustrating an example of a power spectrum of a periodic noise component appearing in an ultrasonic image obtained by the electronic endoscope system according to the first embodiment.

FIG. 10 is a diagram schematically illustrating an example of a power spectrum of a periodic noise component appearing in an ultrasonic image obtained by the electronic endoscope system according to the first embodiment. The noise component generation period is not constant, and fluctuates with a period width in a certain range, and the peak position of the power spectrum in the frequency domain also fluctuates within a certain bandwidth. Assuming that the minimum period of the measured noise component is Tmin and the maximum period is Tmax, the power spectrum varies between the minimum frequency 1/Tmax and the maximum frequency 1/Tmin, as illustrated in FIG. 10.

The noise generation frequency fn of the ultrasonic image illustrated in FIG. 7 as a periodically generated noise component has a value of 14.5 kHz calculated as an example. This frequency is considerably lower than in a case where the signal used by the electronic endoscope 12 or the ultrasonic image processor 30 is several MHz, and the switching frequency of the switching power supply is also several hundred KHz or more.

This kind of periodically generated noise component is considered to be caused by the following factors.

(1) A noise component generated by synchronization of the frequency of a clock signal used by a plurality of constituent devices or a frequency which is an integer multiple of the frequency of a switching signal of a plurality of constituent devices.

(2) Noise component generated by switching power supply (3) Noise component generated by the electronic endoscope insertion portion 54.

(1)

For example, a case will be considered in which the ultrasonic image processor 30 synchronizes the repetition frequency PRF (Pulse Repetition Frequency) of the drive signal of the ultrasonic probe 20 with an integer multiple of the switching frequency of the switching power supply to generate a two-dimensional mode-B image. In a case where the ultrasonic waves are outputted with the switching frequency set to approximately an integer multiple of the PRF, artifacts are likely to occur in the mode-B image.

When transmission and reception are performed between the ultrasonic probe 20 and the ultrasonic image processor 30 with the switching frequency set to approximately an integer multiple of the PRF, switching of the switching power supply is performed within the time the echo signal is detected. Therefore, a noise component derived from switching is generated in each of the echo signals. In a case where a plurality of echo signals obtained from the same ultrasonic beam are added, a noise component caused by switching and generated for each echo signal is added. Therefore, a noise component caused by switching is also added according to the number of echo signals to be added, and this becomes a luminance signal of high luminance through luminance modification, and becomes a noise component that is periodically generated in a mode-B image.

(2)

A switching power supply, for example, a step-down DC/DC converter uses, for example, a MOSFET as a switching element. When the MOSFET is turned on/off, resonance occurs in the loop of the converter due to parasitic inductance and parasitic capacitance, which are parasitic elements, and high-frequency noise is generated, leading to the presence of a noise component in the output of the DC/DC converter via the stray capacitance of the output inductor of the step-down DC/DC converter.

A switching power supply such as a DC/DC converter is provided with a surge absorbing element and a snubber circuit for the purpose of inhibiting a surge/ringing voltage constituting a noise component. However, even if such noise countermeasures are taken, it is difficult to completely eliminate the noise component, and even if the switching frequency is changed, only the generation timing (period) of the noise component is changed and the noise component is not eliminated. Therefore, it is preferable to change the switching frequency from the viewpoint of preventing a phenomenon in which noise components from the plurality of switching power supplies are synchronously superimposed.

Figure 11:
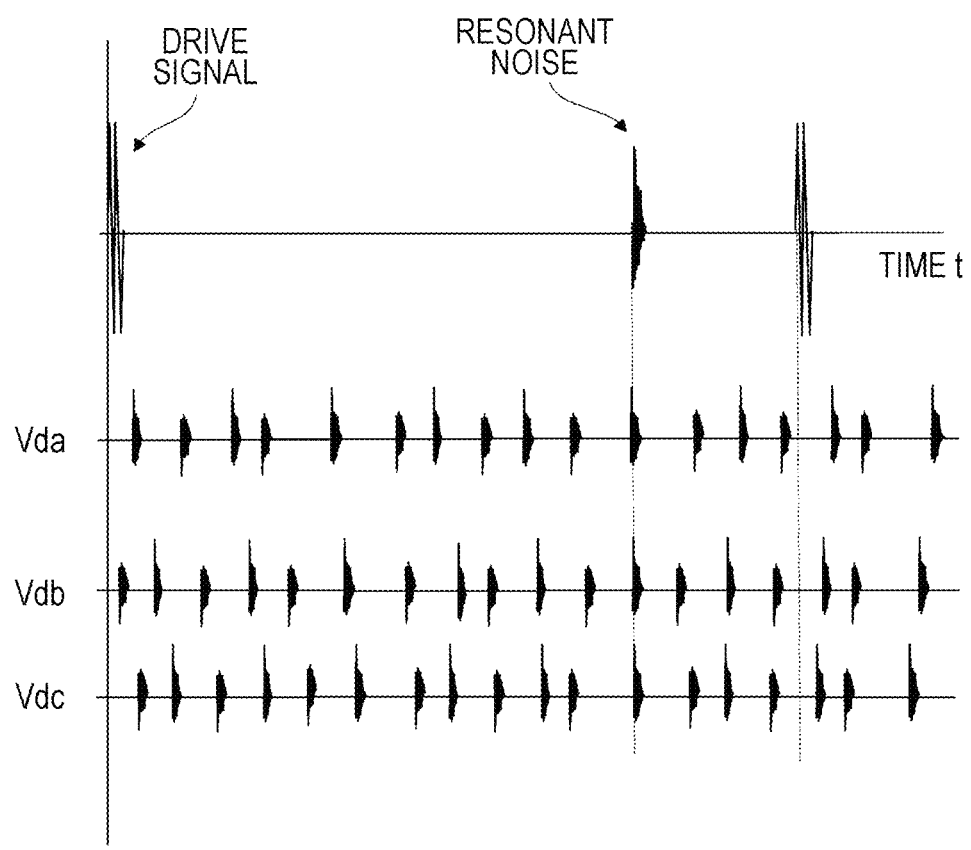
FIG. 11 is a diagram illustrating an example in which noise of a plurality of switching power supplies used in the electronic endoscope system according to the first embodiment is superimposed on an echo signal.

FIG. 11 is a diagram illustrating an example in which noise of a plurality of switching power supplies used in the electronic endoscope system according to the first embodiment is superimposed on an echo signal. For example, noise components superimposed on the DC outputs Vda, Vdb, and Vdc of the three switching power supplies become resonant noise components in synchronization at certain timing, and are superimposed on the echo signal. A resonant noise component is sometimes generated periodically by setting the switching frequency. In this case, the resonant noise component becomes a noise component that is periodically generated in a mode-B image.

(3)

Figure 12:
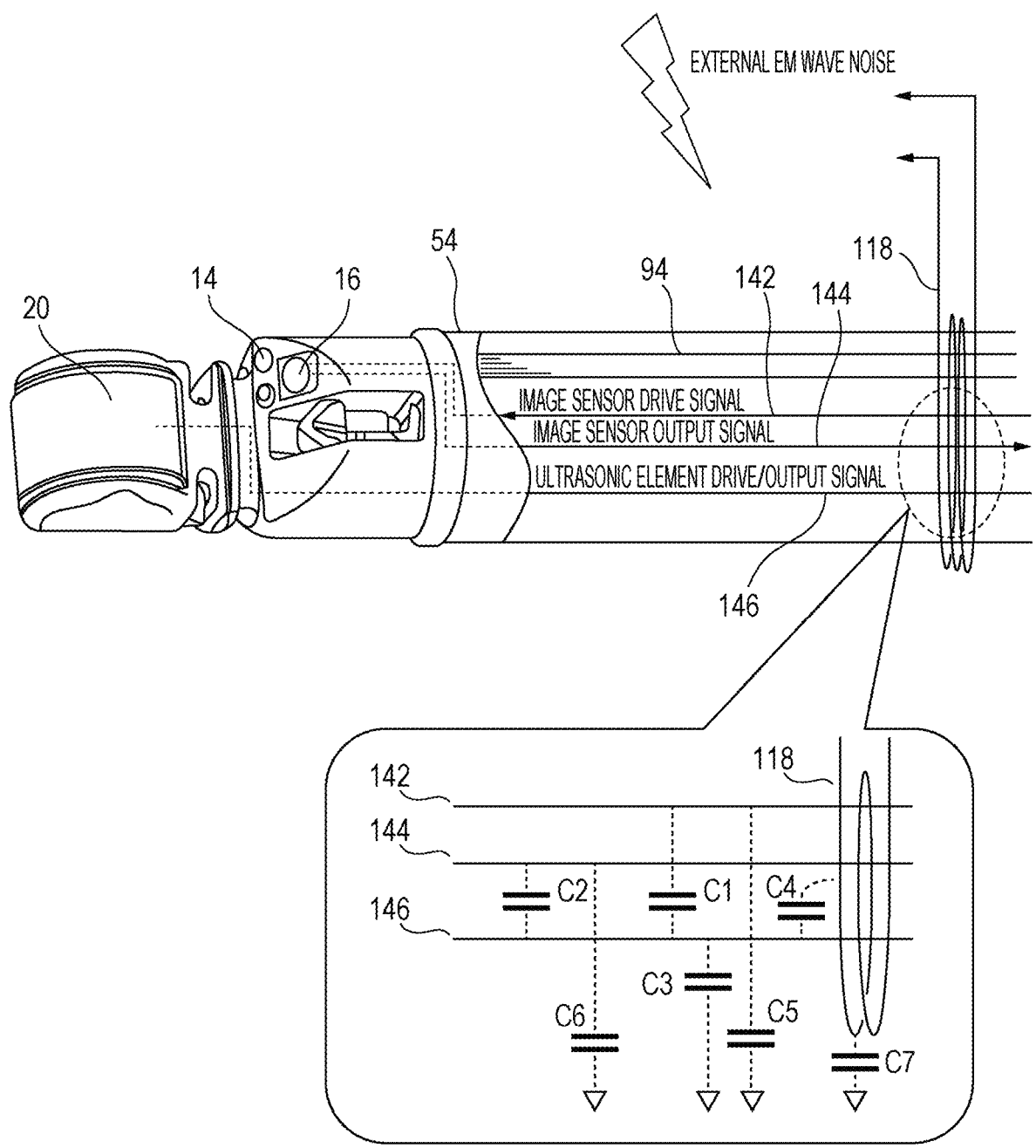
FIG. 12 is a diagram illustrating an example of a noise factor in an electronic endoscope insertion portion used in an electronic endoscope system according to the first embodiment.

FIG. 12 is a diagram illustrating an example of a noise factor in an electronic endoscope insertion portion used in the electronic endoscope system according to the first embodiment. As described above, the illumination unit 14, the image sensor 16, and the ultrasonic probe 20 are provided at the distal tip of the insertion portion 54. Light is transmitted by the light guide 94 to the illumination unit 14. An image sensor drive signal line 142 and an image sensor output signal line 144 are connected to the image sensor 16. The ultrasonic probe 20 is connected to an ultrasonic element drive/output signal line 146 through which a drive signal and an output signal of an ultrasonic element are transmitted. In addition, a transmission coil 118 of an electronic endoscope position measurement device 110 (described subsequently) is wound around the insertion portion 54 as necessary.

Note that, when the electronic endoscope system 10 is used, sometimes an electronic endoscope position measurement device 110 which is capable of using magnetism to specify the position, in a body cavity, of the electronic endoscope 12 inserted into the body cavity. Here, the electronic endoscope position measurement device 110 will be described.

Figure 13:
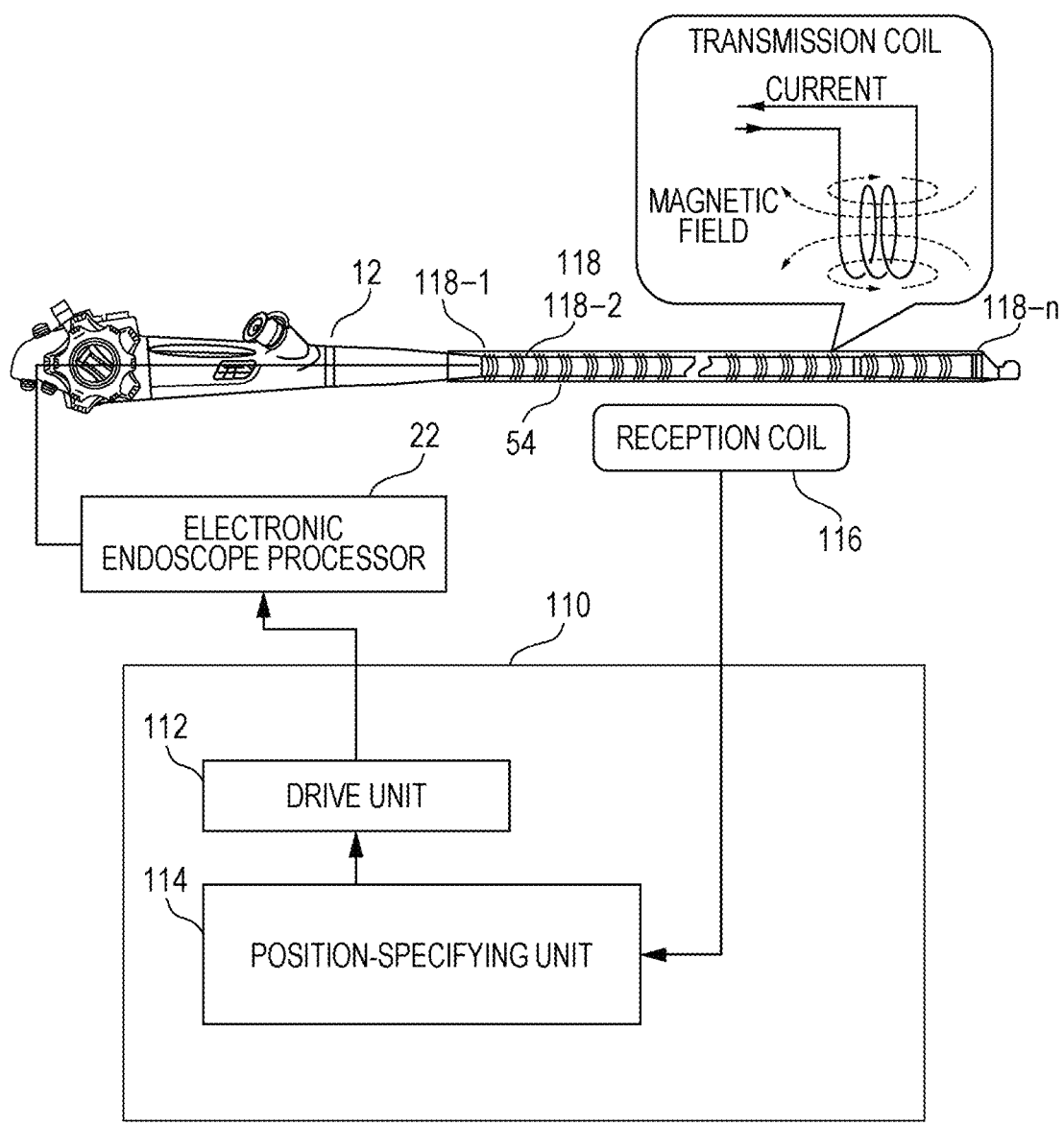
FIG. 13 is a diagram illustrating a schematic example of an electronic endoscope position measurement device which is used in an electronic endoscope system according to the first embodiment.

FIG. 13 is a diagram illustrating a schematic example of an electronic endoscope position measurement device 110 which is used in an electronic endoscope system 10 according to the first embodiment. A plurality of transmission coils 118 used in the electronic endoscope position measurement device 110 are wound around the insertion portion 54 of the electronic endoscope 12 at predetermined intervals, and generate a magnetic field using a current. The plurality of transmission coils 118-1, 118-2, . . . , and 118-$n$ generate a magnetic field at each position when the electronic endoscope 12 is inserted into a body cavity, and receive the magnetic field using a reception coil 116 to measure the position of the endoscope. Note that FIG. 13 illustrates a case where the transmission coils 118 are on the insertion portion 54 and the reception coil 116 is external, but the transmission coils 118 may also be external with the reception coil 116 on the endoscope.

The reception coil 116 includes a plurality of coil blocks and is arranged, for example, beside the bed. Each coil block of the reception coil 116 is wound such that coil surfaces thereof are orthogonal to each other in three directions. The coil detects a signal proportional to the strength of the magnetic field of an axial component orthogonal to the coil surface. The coil block receives the generated magnetic field, converts the magnetic field into a voltage signal, and outputs the voltage signal as a detection result. The operating states of the transmission coils 118 and the reception coil 116 are controlled by the drive unit 112.

Each of the transmission coils 118-1, 118-2, . . . , and 118-$n$ is supplied with a high-frequency sine wave from the drive unit 112 via the captured image processor 22. Each of the transmission coils 118-1, 118-2, . . . , and 118-$n$ emits an electromagnetic wave accompanied by a magnetic field to the surroundings through the application of a sine wave. Note that the drive unit 112 can also individually designate the timing at which each of the transmission coils 118-1, 118-2, . . . , and 118-$n$ generates a magnetic field.

The reception coil 116 receives the magnetic field generated by the transmission coils 118, generates a current from the received magnetic field, and converts the current into a voltage signal. The signal is transmitted from the reception coil 116 to the drive unit 112. The drive unit 112 supplies a signal from the reception coil 116 to a position-specifying unit 114, performs predetermined signal processing such as amplification processing, and then converts the signal into digital data through A/D conversion.

In the specification of the position, the frequency is extracted from the digital data by a Fast Fourier transform, and separated and extracted into magnetic field detection information of the frequency components corresponding to the sine wave of each of the transmission coils 118-1, 118-2, . . . , and 118-$n$. Spatial position coordinates of the transmission coils 118-1, 118-2, . . . , and 118-$n$ provided in the ultrasonic probe 20 are calculated from each of the digital data items of the separated magnetic field detection information. Further, the position-specifying unit 114 connects the position coordinates of the transmission coils 118-1, 118-2, . . . , and 118-$n$ to generate a linear insertion shape image as an electronic endoscope position image.

The length from the coil position located at the inlet portion of the insertion portion to the coil position located at the distal tip of the insertion portion can also be calculated as the insertion length.

In a case where such an electronic endoscope position measurement device 110 is used, the drive signal of the transmission coils 118 may cause generation of a noise component that is periodically generated in the echo signal.

Returning to the description in (3), a stray capacitance exists between the signal line and the transmission coils 118, and noise is induced in the ultrasonic element drive/output signal line 146 through electrostatic coupling. The stray capacitance C1 is a stray capacitance between the image sensor drive signal line 142 and the ultrasonic element drive/output signal line 146. The stray capacitance C2 is a stray capacitance between the image sensor output signal line 144 and the ultrasonic element drive/output signal line 146. The stray capacitance C3 is a stray capacitance between the ultrasonic element drive/output signal line 146 and earth. The stray capacitance C4 is a stray capacitance between the ultrasonic element drive/output signal line and the transmission coils 118. Further, the stray capacitances C5, C6, and C7 are stray capacitances between earth and the image sensor drive signal line 142, the image sensor output signal line 144, and the transmission coils 118.

Due to the stray capacitance, the ultrasonic element drive/output signal line 146 is electrostatically coupled to each line, and a current flowing as a signal of each line is superimposed on the ultrasonic element drive/output signal line 146 as a noise component of a differential mode. Furthermore, the stray capacitances C5 to C7 generated between each signal line and earth become common-mode noise components due to electrostatic coupling, causing a current to flow, and the noise components are superimposed on the ultrasonic element drive/output signal line 146.

In addition, the magnetic field of the transmission coils 118 and external EM wave noise are also superimposed on the ultrasonic element drive/output signal line 146. Further, as illustrated in FIG. 6, there is a possibility that the clock signal 126 of the A/D converter 124 that digitizes echo signals is also superimposed on the ultrasonic element drive/output signal line 146 as EM wave noise. Usually, these noises are minute, but when they are superimposed, they may appear as periodic noise components in the ultrasonic image.

In a connection line to the image sensor 16 and the ultrasonic probe 20 in the electronic endoscope, a noise component is inhibited using a shielding material. Specifically, the noise component is inhibited using reflection loss, absorption loss, and multiple reflection correction of the shielding material. Reflection loss is loss caused by reflection by the shielding material. The absorption loss is loss caused by an induced current flowing when an EM wave is incident on the shielding material. In multiple reflection correction, a noise component is inhibited by utilizing the fact that part of the EM wave that has entered the inside of the shielding material is reflected at the boundary thereof and leaks outside while the reflection is repeated a plurality of times. In multiple reflection correction, correction is performed by taking into account the thickness of the shielding material, the skin effect, and the EM-wave wavelength.

When a countermeasure against noise of the insertion portion 54 which utilizes this kind of shielding material is taken, the outer diameter of the insertion portion 54 becomes large, and thus the insertion portion 54 cannot be sufficiently narrowed. Further, when the drive signal or the output signal is made into a minute signal or a high-frequency signal in order to improve the device performance of the electronic endoscope 12, a noise component problem will likely arise, which may adversely affect image quality enhancement of an ultrasonic image. Therefore, it is difficult to inhibit the noise component using the shielding material.

The periodically generated noise component is not caused by one factor, rather, same is considered to be a complex phenomenon of various noise components. In order to enhance the image quality of the ultrasonic image by inhibiting the periodically generated noise component, it is necessary to detect a noise component which is periodically generated in the echo signal at or above a preset threshold level and inhibit the detected noise component. Here, inhibition of the noise component includes a method of inhibition such that the noise component is not contained in the echo signal, and a method of eliminating the noise pixel by performing image processing on a two-dimensional mode-B image obtained from the echo signal containing the noise component.

Noise Component Inhibition

Figure 14:
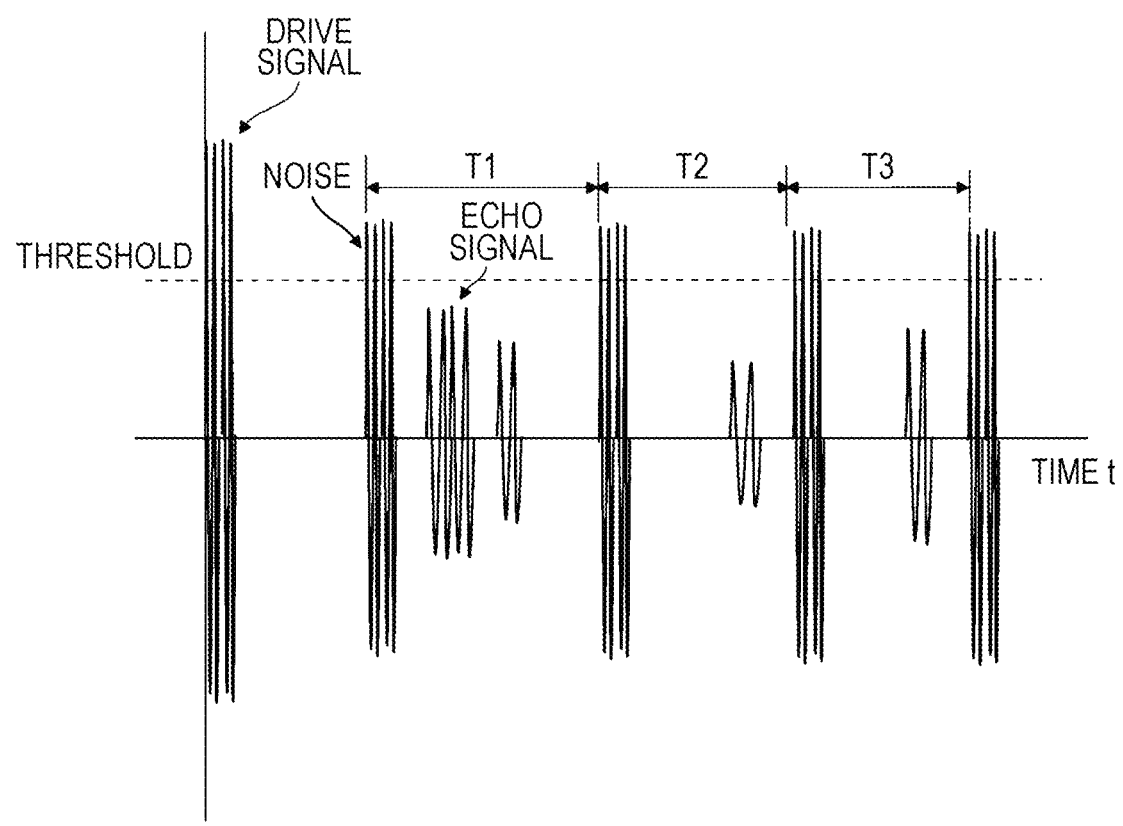
FIG. 14 is a diagram illustrating an example of an echo signal having a superimposed noise component which is generated periodically by the electronic endoscope system according to the first embodiment.

FIG. 14 is a diagram illustrating an example of an echo signal having a superimposed noise component which is generated periodically by the electronic endoscope system according to the first embodiment. The noise component is a waveform that corresponds to a high luminance portion in a mode-B image and that has an amplitude larger than that of the echo signal reflected by the biological tissue using the drive signal of the ultrasonic probe 20. Therefore, the noise detection unit 34 determines and detects a signal equal to or higher than a preset threshold level as a noise component.

Figure 15:
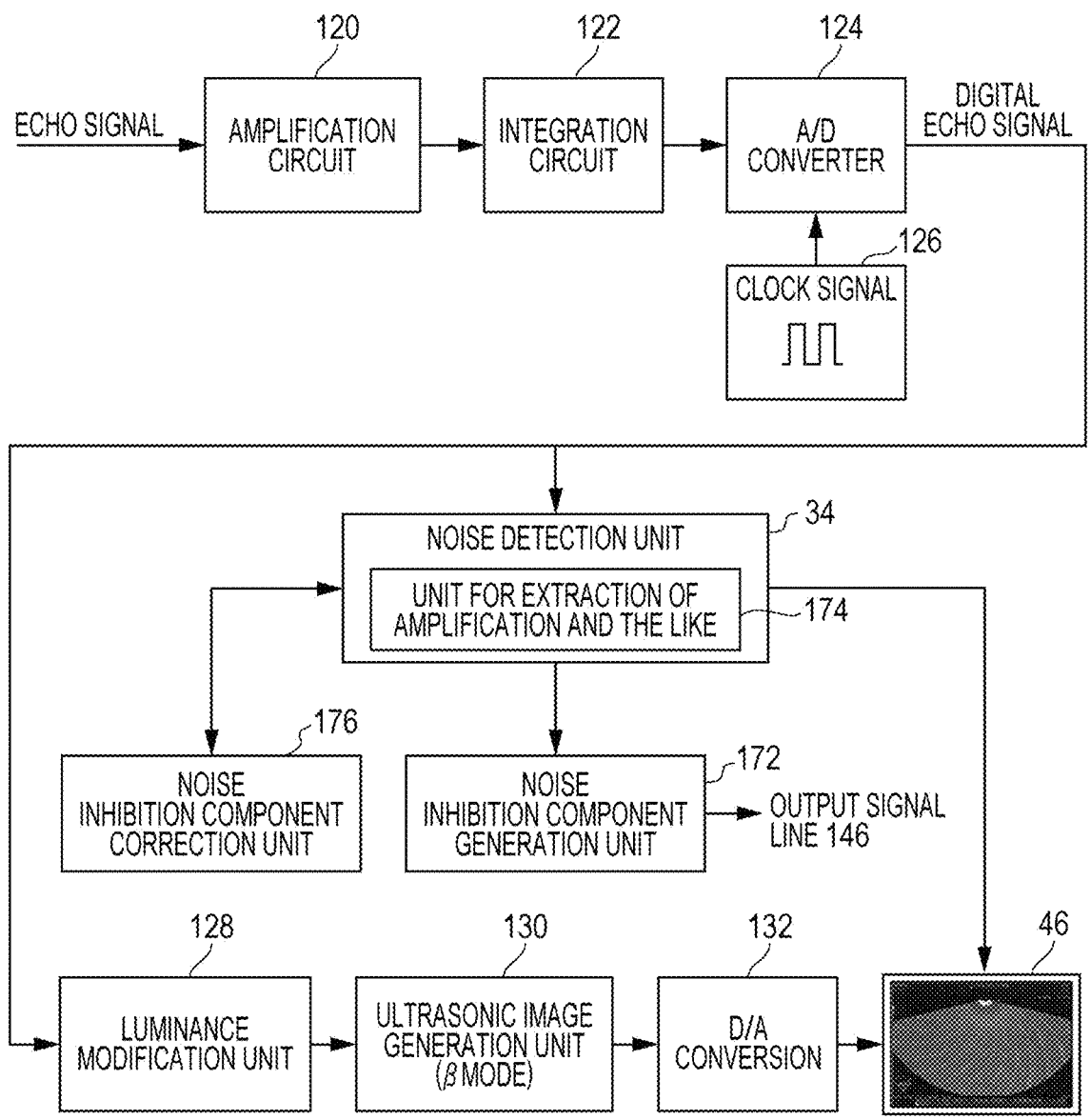
FIG. 15 is a diagram illustrating an example of a noise inhibition unit that is used in the electronic endoscope system according to the first embodiment.

FIG. 15 is a diagram illustrating an example of a method of inhibiting a noise component in an ultrasonic image generated by the electronic endoscope system according to the first embodiment. The echo signal becomes a digital echo signal by passing through the amplification circuit 120, the integration circuit 122, and the A/D converter 124. The noise detection unit 34 presets a threshold for the noise level and determines, as a noise component, a signal at or above the threshold which is contained in the first echo signal.

The unit for extraction of amplitude and the like 174 is provided to the noise detection unit 34. The unit for extraction of amplitude and the like 174 extracts the amplitude, frequency, and phase of the digital echo signal detected as a noise component. The amplitude, frequency, and phase are extracted from the waveform of a mode-A echo signal. The unit for extraction of amplitude and the like 174 determines, as a noise component, a component having a noise level at or above the preset threshold, but instead of such a determination, a component having a spectral peak at or above the set threshold level may also be determined as a noise component by performing frequency analysis using FFT, for example. Here, the unit for extraction of amplitude and the like 174 measures the period (T1, T2, T3, . . . ) of the digital echo signal detected as a noise component. At such time, short periods less than or equal to a certain period are preferably excluded. The periods (T1, T2, T3, . . . ) can be obtained, for example, by specifying, from the waveform of the digital echo signal of a mode-A display, a plurality of noise component generation time points by using a period calculated from the peak frequency of a power spectrum obtained through frequency analysis using FFT of the digital echo signal, and by calculating the time interval between the generation time points. The unit for extraction of amplitude and the like 174 calculates the period width by using the foregoing method. Thus, because the unit for extraction of amplitude and the like 174 calculates the period width and detects the noise component by using the noise generation period and the period width, the detection accuracy is high.

A noise inhibition component generation unit 172 generates a noise inhibition component by utilizing the amplitude, frequency, and phase extracted by the unit for extraction of amplitude and the like 174. The noise inhibition component generation unit 172 outputs the generated noise inhibition component to the ultrasonic element drive/output signal line 146 and applies the noise inhibition component to a second echo signal.

Figure 16:
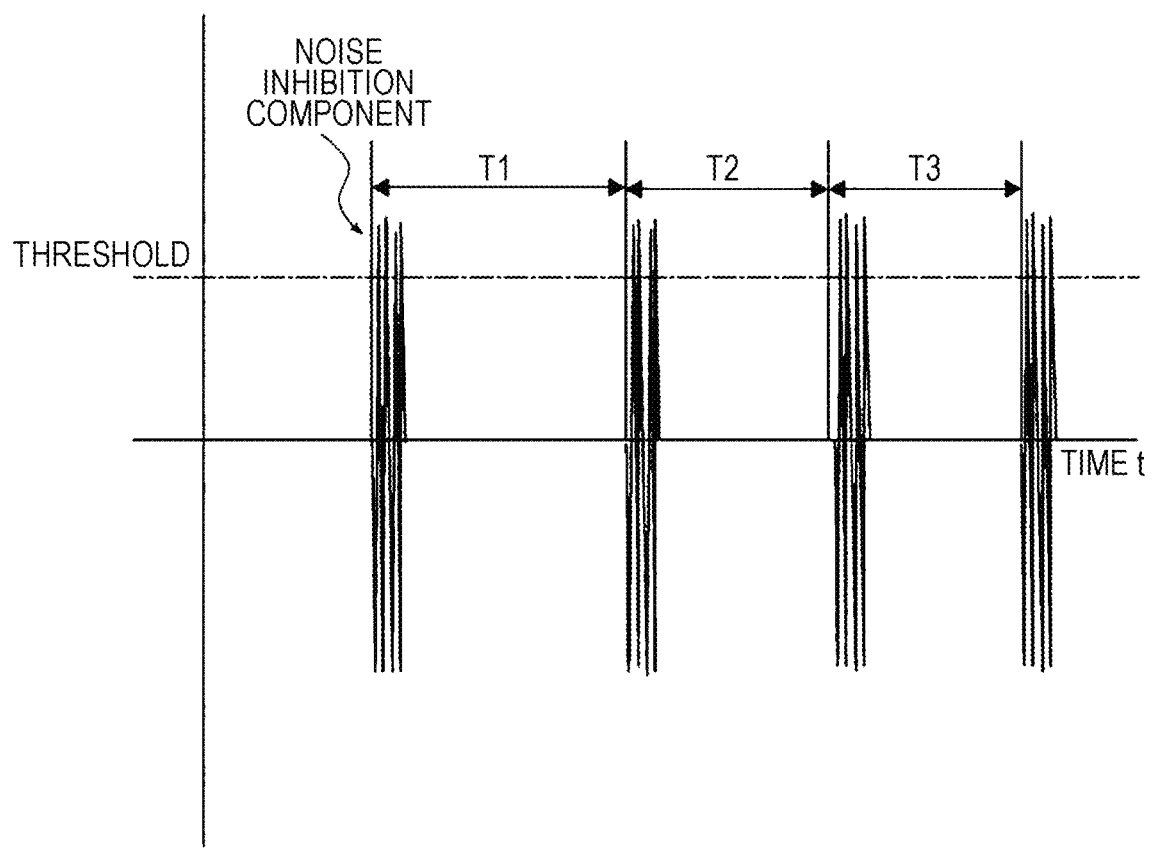
FIG. 16 is a diagram illustrating an example of a noise inhibition component that is used in the electronic endoscope system according to the first embodiment.
Figure 17:
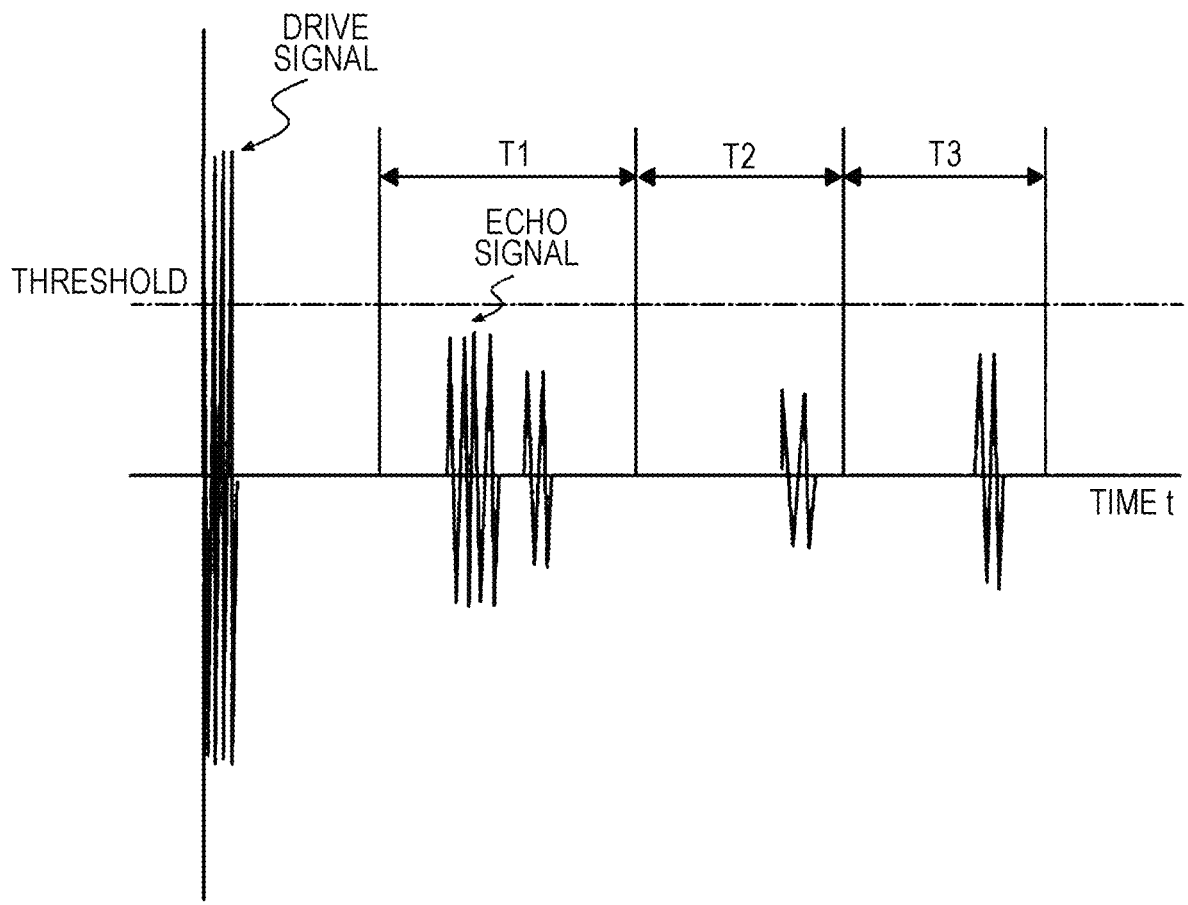
FIG. 17 is a diagram illustrating an echo signal to which the noise inhibition component is added in the electronic endoscope system according to the first embodiment.

FIG. 16 is a diagram illustrating an example of a noise inhibition component, which is a component that inhibits the noise component illustrated in FIG. 14. The noise inhibition component illustrated in FIG. 16 is a component having an opposite phase to that of the noise component illustrated in FIG. 14. The amplitude and frequency of the noise inhibition component illustrated in FIG. 16 are equal to the amplitude and frequency of the noise component. Note that, for example, the amplitude of the noise inhibition component may be smaller than the amplitude of the noise component, other than the example illustrated in FIG. 16. FIG. 17 is a diagram illustrating an example of an echo signal to which a noise inhibition component is added, and illustrates a signal in which the noise inhibition component illustrated in FIG. 16 is added to the echo signal illustrated in FIG. 14.

Thus, by adding the noise inhibition component to the echo signal, the noise component superimposed on the echo signal is canceled, and the generation of the noise component in the echo signal is inhibited. As a result, a high-quality ultrasonic image with few noise components is generated. The addition of the noise inhibition component to the second echo signal is performed while the echo signal is received, except when the drive signal is being transmitted to the ultrasonic probe 20. The noise inhibition component is preferably added by taking all echo signals that are subsequently outputted as second echo signals.

More specifically, in the electronic endoscope system 10, various noises are superimposed on the echo signal outputted from the ultrasonic probe 20, and many of the noises are random noises including harmonic components. Therefore, high image quality is achieved by removing harmonic components. However, it is thought that noise components which are generated periodically are generated in synchronization with many signals and harmonics thereof, and a period in which the harmonics are synchronized is in a low-frequency region and has a large amplitude. Hence, the ultrasonic image processor 30 includes the noise detection unit 34, and determines, as noise, an echo signal which is periodically generated at or above a preset threshold level, and uses the noise inhibition unit 36 to inhibit generation in a subsequent echo signal.

Therefore, in the electronic endoscope system 10, the fact that noise which is periodically generated is a large-amplitude noise component is utilized to detect a noise component by providing a threshold level. However, because the inhibition unit 36 inhibits noise components so that a detected noise component becomes small in the subsequent echo signal, a high-quality ultrasonic image can be obtained.

An echo signal to which the noise inhibition component has been added is preferably corrected by a noise inhibition component correction unit 176 (FIG. 15). The correction is performed by adjusting at least any one of an amplitude, a frequency, and a phase of the noise inhibition component so that the level of the noise component is reduced in the echo signal to which the noise inhibition component is added. If a noise component that is generated periodically has a period width, there is a risk of a noise component being generated in a subsequent echo signal in a generation period which is different from the generation period of the detected noise component. Further, the amplitude, frequency, and phase of the noise component will also likely change after detection due to some factor, for example, the start of use of a device using an AC power supply as a power source in another room or the like. For this reason, even if a noise inhibition component is generated on the basis of the detected noise component and added to the subsequent echo signal, noise component generation may not be sufficiently inhibited. Therefore, the noise inhibition component correction unit 176 preferably corrects the noise inhibition component added to the echo signal to reduce the noise component in the echo signal to which the noise inhibition component is added. When the noise component is already inhibited by the addition of the noise inhibition component, the noise level is further reduced. By feedback-adjusting the noise component in this manner, in the echo signal to which the noise inhibition component is added, components other than the echo signal reflected by the biological tissue can be minimized, thereby maintaining the advantageous effect of inhibiting noise component generation.

Specifically, the correction of the noise inhibition component performs processing to reduce the signal level of components corresponding to noise components in a first echo signal detected by the unit for extraction of amplitude and the like 174 among the second echo signals to which the noise inhibition component has been added. Such processing is performed, for example, by changing the amplitude, frequency, and phase of the noise inhibition component.

The noise detection unit 34 preferably detects noise components by targeting echo signals in which the noise inhibition component has been corrected. In a case where a noise component contained in an echo signal cannot be inhibited even when the noise inhibition component is corrected, for example, it is possible to notify the practitioner that noise has been generated. For this reason, when a noise component is detected in an echo signal to which the noise inhibition component has been added, the ultrasonic image display unit 46 preferably displays a display for prompting noise component inhibition on the display screen. By implementing such a display, it is possible to notify the practitioner that there is noise and to prompt the practitioner to take measures for inhibiting the noise component, so that diagnosis using the ultrasonic image is not affected. The display for prompting the practitioner to inhibit a noise component is a display for prompting the practitioner to take measures for inhibiting the noise component. Examples of such measures include contacting the company performing the maintenance and repair of the electronic endoscope system 10, and changing the connection destination (outlet) of the plug of the AC power input unit 48.

Note that the threshold level used to detect noise components in the second echo signals has the same value as the threshold level used to detect noise components in the first echo signal. The noise inhibition component is preferably corrected during reception of the echo signal to which the noise inhibition component has been added except when the drive signal is transmitted to the ultrasonic probe 20.

In the foregoing embodiment, noise components are detected using a preset threshold or using frequency analysis. Alternatively, noise components may be detected using a prediction model subjected to machine learning, that is, using artificial intelligence (AI).

In detection using AI, the noise detection unit 34 extracts a feature amount through machine learning using, as training data, a learning ultrasonic image without an echo signal in which a noise component is periodically generated and a learning ultrasonic image in which a noise component is periodically generated. As a result, the presence or absence of a periodic noise component can be learned in advance. Based on the learning result, the presence or absence of a periodic noise component of an inputted ultrasonic image is determined. It is also preferable to use an ultrasonic image in which a periodically generated noise component is detected by the noise detection unit 34 or the unit for extraction of amplitude and the like 174 as the training ultrasonic image in which the noise component is periodically generated.

Figure 18:
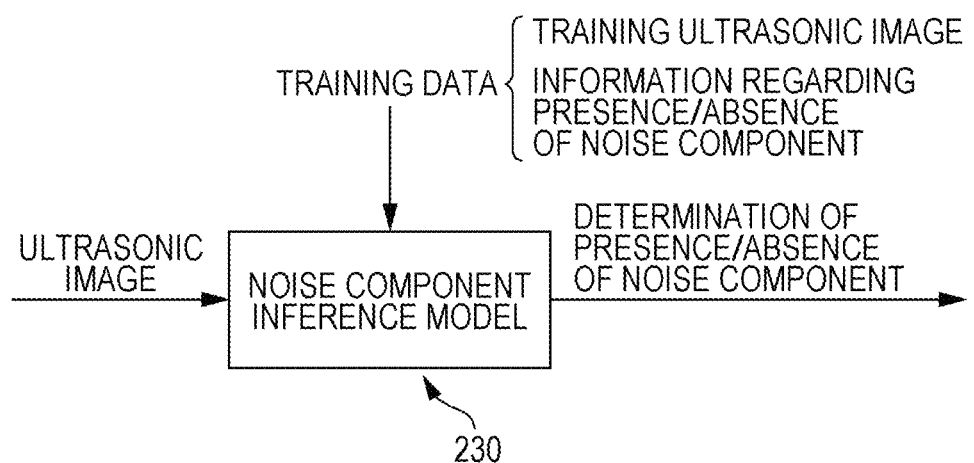
FIG. 18 is a diagram illustrating an example of a process of learning by artificial intelligence (AI) and determining the presence or absence of a periodically generated noise component in the electronic endoscope system according to the first embodiment.

FIG. 18 is a diagram illustrating an example of a process of learning using artificial intelligence (AI) and determining the presence or absence of a periodically generated noise component in the electronic endoscope system according to the first embodiment. A noise component inference model 230 is created by extracting a feature amount through machine learning from the training ultrasonic image to which information on the presence or absence of the noise component is supplied. By inputting the ultrasonic image to the noise component inference model 230, the noise component inference model 230 is capable of determining the presence or absence of a noise component from the feature amount extracted therein. Examples of the feature amount include the amplitude of the noise component, the periodicity of the noise component, and the spread of the noise component.

The noise component inference model 230 of the noise detection unit 34 is created using a neural network, for example. As the neural network, for example, a convolutional neural network widely applied in image recognition is suitably used.

Figure 19:
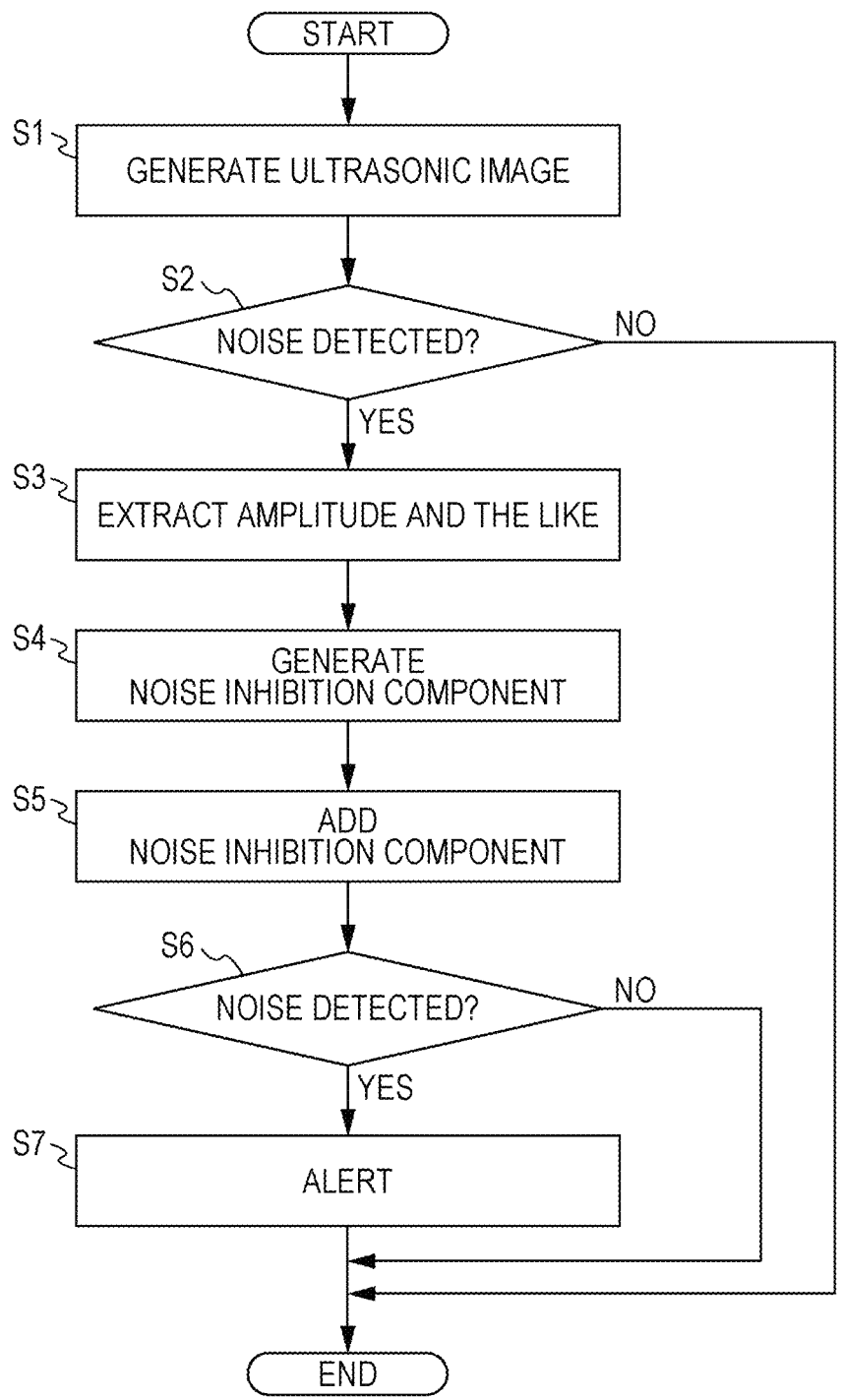
FIG. 19 is a diagram illustrating an example of the operation flow of noise inhibition performed in the electronic endoscope system according to the first embodiment.

FIG. 19 is a diagram illustrating a noise inhibition operation flow. First, in step S1, an ultrasonic image is generated. The ultrasonic image is generated by the ultrasonic image generation unit 130 after an echo signal from the ultrasonic probe 20 is converted into grayscale pixels by the luminance modification unit 128. In step S2, periodic noise is detected. In the detection of noise, a signal greater than or equal to a predetermined threshold is detected as noise. When no noise is detected, the processing ends.

When noise is detected, the amplitude, frequency, and phase of the noise component are extracted in step S3. The extraction is performed by the unit for extraction of amplitude and the like 174. In step S4, a noise inhibition component is generated using the amplitude, frequency, and phase of the extracted noise component. In step S5, the generated noise inhibition component is added to the second echo signal. The noise inhibition component is generated and added by the noise inhibition component generation unit 172. In step S6, the noise inhibition component is corrected in the second echo signal to which the noise inhibition component has been added, and in order to confirm whether the noise has been corrected, the noise detection unit 34 detects noise greater than or equal to the threshold level. When noise is detected, a warning is issued in step S7, and the processing ends. The warning is displayed on the ultrasonic image display unit 46. In this case, the practitioner is notified of the presence of noise so as not to affect diagnosis using the ultrasonic image. When no noise is detected, the processing ends.

As described with reference to FIG. 12, in the electronic endoscope system described above, external noise is superimposed on the ultrasonic element drive/output signal line 146 due to the effect of electrostatic coupling and/or electromagnetic coupling. Therefore, in the electronic endoscope system of the first embodiment, an antenna is provided near the shield (external conductor) of the cable which includes the ultrasonic element drive/output signal line 146 in order to detect external noise superimposed on the ultrasonic element drive/output signal line 146. A noise inhibition component is generated using an external noise component (amplitude, frequency, phase) detected by the antenna, and the noise inhibition component is applied by the antenna to the shield of the cable containing the ultrasonic element drive/output signal line 146. As a result, the external noise component in the shield is canceled, and the external noise component superimposed on the ultrasonic element drive/output signal line 146 is reduced.

Figure 20:
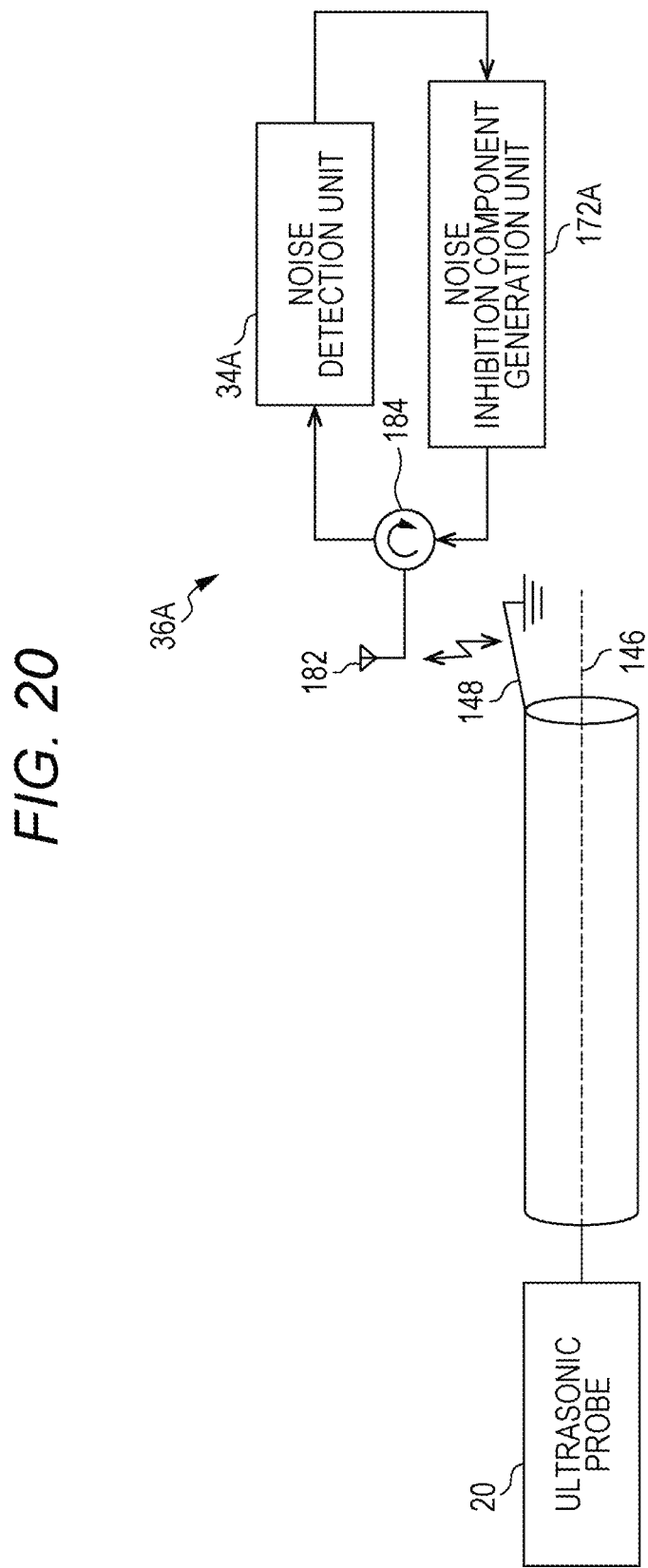
FIG. 20 is a diagram illustrating an example of the noise inhibition unit that is used in the electronic endoscope system according to the first embodiment.

FIG. 20 conceptually illustrates a configuration example for reducing external noise superimposed on the ultrasonic element drive/output signal line 146 in the electronic endoscope system of the first embodiment.

As illustrated in FIG. 20, in the electronic endoscope system of the first embodiment, the antenna 182 is arranged in the vicinity of the shield 148 of the cable of the ultrasonic element drive/output signal line 146 extending from the ultrasonic probe 20. Note that the shield 148 is grounded in the ultrasonic image processor 30 or the electronic endoscope 12.

In order to prevent the radio waves emitted from the antenna 182 from being superimposed on the ultrasonic element drive/output signal line 146, for example, it is preferable to employ measures such as a measure to secure the distance between the antenna 182 and the ultrasonic element drive/output signal line 146, or a measure to make the orientation of the radio waves emitted from the antenna orthogonal to the direction of extension of the ultrasonic element drive/output signal line 146.

In the electronic endoscope system illustrated in FIG. 20, in addition to the antenna 182, a circulator 184, a noise detection unit 34A, and a noise inhibition component generation unit 172A (an example of the noise inhibition unit) constitute a noise inhibition unit 36A as a whole. The noise inhibition unit 36A may be provided in the ultrasonic image processor 30 or may be provided in the electronic endoscope 12. Alternatively, part of the configuration of the noise inhibition unit 36A may be provided to one of the ultrasonic image processor 30 and the electronic endoscope 12, and part of the configuration of the noise inhibition unit 36A may be provided to the other of the ultrasonic image processor 30 and the electronic endoscope 12.

The circulator 184 is provided to switch transmission and reception by the antenna 182. Provision of the circulator 184 is not essential, and the transmission antenna and the reception antenna may be provided separately.

The antenna 182 is, for example, a loop antenna or a monopole antenna, and is disposed near the shield 148 so as to obtain favorable electromagnetic coupling. As a result, the noise detection unit 34A detects an external noise component superimposed on the shield 148 via the antenna 182, and acquires the amplitude, frequency, and phase of the external noise component.

Note that the noise detection unit 34A may perform processing corresponding to the amplification circuit, the integration circuit, and the A/D converter in FIG. 15 on the reception signal (signal corresponding to the external noise component) from the antenna 182 as pre-processing before noise detection.

Similarly to the above-described noise inhibition component generation unit 172, the noise inhibition component generation unit 172A generates a noise inhibition component that is a component having an opposite phase to the detected external noise component. The amplitude and frequency of the noise inhibition component are preferably equal to the amplitude and frequency of the external noise component, but the amplitude of the noise inhibition component may be smaller than the amplitude of the external noise component.

The noise inhibition component generation unit 172A preferably adjusts at least one of the amplitude, the frequency, and the phase of the noise inhibition component so that the level of the external noise component is minimized.

The noise inhibition component generated by the noise inhibition component generation unit 172A is applied by the antenna 182 to the shield 148 of the ultrasonic element drive/output signal line 146. As a result, external noise is canceled in the shield 148, and noise superimposition on the ultrasonic element drive/output signal line 146 can be inhibited. As a result, a high-quality ultrasonic image can be obtained.

There are no limitations on the timing for switching between the noise detection period (that is, the period of reception by the antenna 182) and the period for applying the noise inhibition component (that is, the period of transmission by the antenna 182). In the first embodiment, the noise detection is performed at predetermined time intervals, and in a period in which the noise detection is not performed, the noise inhibition component based on the immediately preceding noise detection result is applied to the shield 148.

Note that, after the noise inhibition component is applied, an external noise component which is superimposed on the shield 148 is detected, and in a case where the noise level (for example, amplitude) of the external noise component does not become less than or equal to a predetermined threshold, for example, a warning may be displayed on the ultrasonic image display unit 46.

The electronic endoscope system of the present invention is described above in detail, but the electronic endoscope system of the present invention is not limited to the foregoing embodiment, and may of course be modified or altered in various ways in a range not deviating from the scope and spirit of the present invention.

The present invention relates to Japanese Patent Application No. 2020-159687 filed with the Japan Patent Office on Sep. 24, 2020, entire content of which is incorporated by reference in the specification.

The invention claimed is:

1. An electronic endoscope system configured to acquire an ultrasonic image, the electronic endoscope system comprising:
   an electronic endoscope having, at a distal tip thereof, an ultrasonic probe configured to repeatedly apply ultrasonic waves to biological tissue to sequentially obtain echo signals; and
   an ultrasonic image processor configured to
      process the echo signals outputted from the ultrasonic probe to generate an ultrasonic image,
      detect a noise component which is contained in a first echo signal among the echo signals and which is periodically generated at or above a preset threshold level,
      generate a noise inhibition component which, by being added to a second echo signal outputted after the first echo signal, inhibits generation of the noise component in the second echo signal, and adds the noise inhibition component to the second echo signal, and
      adjust at least any one of an amplitude, a frequency, and a phase of the noise inhibition component so that the level of the noise component is reduced in the second echo signal to which the noise inhibition component is added.

2. The electronic endoscope system according to claim 1, wherein the noise inhibition component is a component having an opposite phase to that of the noise component.

3. The electronic endoscope system according to claim 1, wherein the processor is further configured to detect the noise component contained in the second echo signal to which the noise inhibition component has been added.

4. The electronic endoscope system according to claim 3, wherein the electronic endoscope system further comprises a display configured to display the ultrasonic image on a display screen, and when the noise component is detected in the second echo signal to which the noise inhibition component has been added, the display causes the display screen to render a display prompting inhibition of the noise component.

5. The electronic endoscope system according to claim 1, wherein the processor is further configured to
calculate a noise generation period in which the noise component is periodically generated,
calculate a period width from a minimum value and a maximum value of the noise generation period, and
detect the noise component by using the noise generation period and the period width.

6. The electronic endoscope system according to claim 1, wherein the processor is further configured to
create a noise component inference model in which the presence or absence of the noise component is machine-learned in advance by using, as training data, a training ultrasonic image without the noise component and a training ultrasonic image having the noise component, and
determine the presence or absence of the noise component by inputting the ultrasonic image generated by the processor to the noise component inference model.

7. An electronic endoscope system configured to acquire an ultrasonic image, the electronic endoscope system comprising:
an electronic endoscope having, at a distal tip thereof, an ultrasonic probe configured to repeatedly apply ultrasonic waves to biological tissue to sequentially obtain echo signals and a processor; and
an ultrasonic image processor configured to process the echo signals outputted from the ultrasonic probe to generate an ultrasonic image,
wherein either one of the processor of the electronic endoscope and the ultrasonic image processor is configured to
detect an external noise component that is superimposed on the echo signals transmitted by a cable outputted from the ultrasonic probe,
generate a noise inhibition component which inhibits the external noise component, and that applies the noise inhibition component to the echo signals transmitted by the cable, and
adjust at least any one of an amplitude, a frequency, and a phase of the noise inhibition component so that the level of the noise component is reduced in the second echo signal to which the noise inhibition component is added.

8. The electronic endoscope system according to claim 7, wherein the noise inhibition component is a component having an opposite phase to that of the external noise component.

9. The electronic endoscope system according to claim 7, wherein either one of the electronic endoscope and the ultrasonic image processor comprises an antenna that acquires the external noise component from the echo signals transmitted by the cable.

* * * * *